US010421782B2

(12) United States Patent
Baroni et al.

(10) Patent No.: US 10,421,782 B2
(45) Date of Patent: Sep. 24, 2019

(54) CYCLIC CATIONIC PEPTIDES WITH ANTIMICROBIAL ACTIVITY

(71) Applicant: I.C.F. S.R.L., Palazzo Pignano (CR) (IT)

(72) Inventors: Maria Cristina Baroni, Parma (IT); Clotilde Silvia Cabassi, Parma (IT); Antonello Romani, Parma (IT)

(73) Assignee: ICF S.r.l., Palazzo Pignano (CR) (IT)

( * ) Notice: Subject to any disclaimer, the term of this patent is extended or adjusted under 35 U.S.C. 154(b) by 148 days.

(21) Appl. No.: 14/654,350

(22) PCT Filed: Dec. 30, 2013

(86) PCT No.: PCT/IB2013/002893
§ 371 (c)(1),
(2) Date: Jun. 19, 2015

(87) PCT Pub. No.: WO2014/102596
PCT Pub. Date: Jul. 3, 2014

(65) Prior Publication Data
US 2016/0083427 A1    Mar. 24, 2016

Related U.S. Application Data

(60) Provisional application No. 61/901,680, filed on Nov. 8, 2013.

(30) Foreign Application Priority Data
Dec. 28, 2012    (IT) .................. MI2012A002263

(51) Int. Cl.
  *C07K 7/08*   (2006.01)
  *A61K 38/10*  (2006.01)
  *A61K 38/04*  (2006.01)
  *A61K 38/16*  (2006.01)
  *C07K 7/50*   (2006.01)
  *C07K 14/00*  (2006.01)
  *A61K 38/00*  (2006.01)

(52) U.S. Cl.
CPC ............. *C07K 7/08* (2013.01); *A61K 38/04* (2013.01); *A61K 38/10* (2013.01); *A61K 38/16* (2013.01); *C07K 7/50* (2013.01); *C07K 14/00* (2013.01); *A61K 38/00* (2013.01); *Y02A 50/401* (2018.01); *Y02A 50/469* (2018.01); *Y02A 50/473* (2018.01); *Y02A 50/475* (2018.01); *Y02A 50/481* (2018.01)

(58) Field of Classification Search
CPC .................................. A61K 38/14; C07K 7/64
See application file for complete search history.

(56) References Cited

U.S. PATENT DOCUMENTS

| | | | | |
|---|---|---|---|---|
| 6,307,016 B1 * | 10/2001 | Lehrer | ........... | A01N 37/46 530/317 |
| 6,538,155 B1 | 3/2003 | Melman | | |
| 7,588,752 B2 | 9/2009 | Reynolds | | |
| 2002/0147301 A1 | 10/2002 | Lehrer et al. | | |
| 2003/0147906 A1 * | 8/2003 | Friede | ........... | C07K 16/00 424/186.1 |
| 2006/0069022 A1 | 3/2006 | Bobek | | |
| 2007/0003538 A1 | 1/2007 | Madhyastha | | |

FOREIGN PATENT DOCUMENTS

| | | |
|---|---|---|
| WO | 9702287 A1 | 1/1997 |
| WO | 2009037183 A2 | 3/2009 |

OTHER PUBLICATIONS

Masuda, Masao (Biochemical and Biophysical Research Communications 189(2), 845-50, 1992).*
Davidson (Nucleic Acids Research 39(1), 248-256, 2011).*
Betts et al. "Amino Acid Properties and Consequences of Substitutions", Bioinformatics for Geneticists. Edited by Barnes and Gray, 2003; Chapter 14, pp. 289-316 (Year: 2003).*
Romani et al., "In vitro activity of novel in silico-developed antimicrobial peptides against a panel of bacterial pathogens", Journal of Peptide Science, published online Jul. 26, 2013, pp. 554-565 (Year: 2013).*
A. A. Romani et al: "In vitro activity of novel in silica-developed antimicrobial peptides against a panel of bacterial pathogens". Journal of Peptide Science, vol. 19, No. 9, Jul. 26, 2013 (Jul. 26, 2013), pp. 554-565. XP055119521.
Masuda M et al: "A novel anti-HIV synthetic peptide. T-22 ([Tyr<5,12>. Lys<7>]-polyphemusin 11)", Biochemical and Biophysical Research Communications, Academic Press Inc. Orlando, FL, US, vol. 189. No. 2.
WO2009037183—English Machine Translation.
A. A. Romani, et al., "In vitro activity of novel in silico-developed antimicrobial peptides against a panel of bacterial pathogens", Journal of Peptide Science, vol. 19, No. 9, Sep. 26, 2013, pp. 554-565.

(Continued)

Primary Examiner — Lianko G Garyu
(74) Attorney, Agent, or Firm — King & Schickli, PLLC

(57) ABSTRACT

A series of cationic cyclic peptides, useful for the treatment of infectious diseases in both human and veterinary clinical/surgical environment are described herein. The peptides of the invention have a length of 15 to 21 amino acids, and show a sequence A-B-C-D-C'-B'-A', wherein units A and A' correspond to —NH$_2$ terminal and —COOH terminal regions; units B and B' correspond to cyclizable amino acids containing sulfur; units C and C are sequences of 5 amino acids selected among hydrophobic amino acids, basic amino acids and amino acids forming hydrogen bonds; unit D is a dipeptide consisting of glycine and one basic amino acid. Said peptides show significant antibacterial activity, associated with high stability and resistance to the action of bacterial endopeptidases, and weak or null toxicity against eukaryotic cells.

13 Claims, 4 Drawing Sheets
Specification includes a Sequence Listing.

(56) References Cited

OTHER PUBLICATIONS

Giuseppantonio Maisetta, et al., "Activity of Human [beta]-Defensin 3 Alone or Combined with Other Antimicrobial Agents against Oral Bacteria", Antimicrobial Agents and Chemotherapy, American Society for Microbiology, vol. 47, No. 10, Oct. 1, 2003, pp. 3349-3351.
Kim, S. S., et al., : "Synergistic Inhibitory Effect of Cationic Peptides and Antimicrobial Agents on the Growth of Oral Streptococci", Caries Research, S. Karger AG, Basel, CH, vol. 37, Jan. 1, 2003, pp. 425-430.
Reichel M., et al., : "Skin bacteria after chlorhexidine exposure—is there a difference in response to human [beta]-Defensin-3?", European Journal of Clinical Microbiology & Infectious Diseases, Springer, Berlin, DE, vol. 29, No. 6, Mar. 27, 2010, pp. 623-632.
Keun-Hyeung, Lee, et al., : "Antimicrobial Activity and Conformation of Gaegurin-6 Amide and Its Analogs", Peptides, vol. 19, No. 10, Jan. 1, 1998, pp. 1653-1658.
Pusateri, C. R., et al., : "Sensitivity of Candida albicans biofilm cells grown on denture acrylic to antifungal proteins and chlorhexidine", Archives of Oral Biology, Pergamon Press, Oxford, GB, vol. 54, No. 6, Jun. 1, 2009, pp. 588-594.
Andre C. Amaral et al: "Predicting antimicrobial peptides from eukaryotic genomes: In silico strategies to develop antibiotics", Peptides, vol. 37, No. 2, Oct. 1, 2012, pp. 301-308.
Masuda, M. et al.; "A novel anti-HIV synthetic peptide. T-22 ([Tyr<5,12>.Lys<7>]-polyphemusin 11)", Biochemical and Biophysical Research Communications, Academic Press Inc., Orlando, FL. vol. 189. No. 2, 1992.
Su-Jin Kang et al.; "Antimicrobial peptides: Their physicochemical properties and therapeutic application", Archives of Pharmacal Research, Pharmaceutical Society of Korea, Heidelberg vol. 35. No. 3, Apr. 5, 2012 (Apr. 5, 2012).
Tamamura H et al.; "Pharmacophore identification of a chemokine receptor (CXCR4) antagonist, T22 ([Tyr<5,12>, Lys<7>]-polyphemusin II), which specifically blocks T cell-line-tropic HIV-1 infection". Bioorganic & Medicinal Chemistry, Pergamon, GB, vol. 6, No. 7, Jul. 1, 1998 (Jul. 1, 1998).
Guardabassi, G., et al., In vitro antimicrobial activity of a commercial ear antiseptic containing chlorhexidine and Tris-EDTA, Veterinary Dermatology, vol. 21, 282-286, 2009.
Written Opinion and International Search Report for PCT/IB2015/054790 dated Oct. 2, 2015 (from 2108-020).

* cited by examiner

CYCLIC CATIONIC PEPTIDES WITH ANTIMICROBIAL ACTIVITY

This application is the national stage of international patent application no. PCT/IB2013/002893 filed on Dec. 30, 2013 which in turn claims priority from U.S. Provisional Patent Appl. S.N. 61/901,680 filed on Nov. 8, 2013 and from Italian Appl. No. MI2012A002263 filed on Dec. 28, 2012. The disclosures of each document are incorporated herein by reference in their entirety.

FIELD OF THE INVENTION

The present invention provides a series of cyclic or cyclizable cationic peptides with antimicrobial activity, characterized by low or not detectable cytotoxicity against cells of superior organisms, that are cytostatic or cytotoxic against at least one Gram-negative and/or Gram-positive bacterium and fungus (comprising yeasts) derived from reference strains or clinical isolates.

STATE OF THE ART

Treatment of bacterial infections with antibiotics represents one of the pillars of human medicine. Development and employment of antibiotics, starting from the second half the XX century, have revolutionized the approach to treatment and prevention of infectious diseases and infections considered incurable in the past.

The need for new and ever more efficient antimicrobial compounds has induced pharmaceutical companies to concentrate their efforts towards the development of new molecules, with the result of making available, starting from the beginning of the sixties of the last century, over 200 different antimicrobial compounds (Overbye and Barrett, Drug Discovery Today, 10: 45-52, 2005).

However, despite resources and energies have been invested in order to increase the knowledge of the resistance mechanisms, and in the research of ever more efficient molecules, at the moment, the development of drug-resistance to antibiotics is faster than the discovery of new classes of molecules.

The inability of pharmaceutical industries to identify new antimicrobial compounds is clear from the dramatic reduction in the number of new marketed molecules. In fact, while from 1983 to 2001 the FDA (Food and Drug Administration) approved 47 new compounds for clinical use, in the period 1998-2005 only 9 compounds were licensed for clinical use (Overbye and Barrett, see previous reference).

Antibiotic-resistance, defined as the emergence (and the propagation) of factors of bacterial resistance to antibiotics, is triggered by the selective pressure exerted on microbial populations by an excessive and/or improper use of these drugs. Infections by resistant bacteria cause estimated health costs between 10 and 15 billion dollars per year in the USA only, with increased morbidity, mortality and costs associated to the disease (Prevention effectiveness: A guide to decision analysis and economic evaluation. 2nd Edition. Editors: Haddix A C, Teutsch S M, Corso P S., New York: Oxford University Press 2003:345-57). A paper, recently published on Clinical Infectious Diseases, highlighted a health cost per patient affected by antibiotic-resistant infections (ARI) evaluable between 18,000 and 29,000 dollars associated with a mean increase of hospitalization between 6 and 12 days. Also mortality rates for these patients result about 2-2.5 times higher compared with non-ARI patients (R. R. Roberts et al., 2009 Clin Infect Dis; 49:1175-84).

Today this problem has become a veritable public health priority on a global scale, also due to the appearance of pathogens simultaneously resistant to several antibiotics (multidrug resistance, or heterogeneous resistance), de facto reducing the possibility of an efficient treatment (WHO Global Strategy for Containment of Antimicrobial Resistance. Geneva, World Health Organization, 2001, WHO/CDS/CSR/DRS/2001.2). It should be pointed out that heterogeneous antibiotic-resistance often involves health structures. These multi-resistant microorganisms deriving from hospital acquired infections can be transmitted in a community in various ways among which: ventilation and aeration systems, water flow, treatment of tissues and laboratory samples, inadequate hygiene of personnel and environment, surgical procedures and invasive devices (Eggimann, Clin Microbiol Infect 2001; 7:91; Pittet, The Lancet 2000; 356:1307; Hugonnet, Clin Microbiol Infect 2000; 6:350; Pittet, Swiss-NOSO 2001; 8:25).

Among the major problems, meticillin-resistance in *S. aureus* should be mentioned ("Celbenin"-resistant staphylococci. Br Med J, 1:124-25, 1961), which prevalence in Italy has reached a constant incidence around 40%, and is among the highest in Europe (Antimicrobial resistance surveillance in Europe 2009. Annual Report of the European Antimicrobial Resistance Surveillance Network (EARS-Net). Stockholm, European Centre for Disease Prevention and Control (ECDC), 2010). Penicillin-resistance in *S. pneumoniae* reaches a frequency higher than 20% in some European countries and in the United States, and it even exceeds 50% in the Far East. Recently, high macrolide-resistance has been observed in this microorganism, with values reaching 30%, with an increasing trend. In the genus *Enterococcus* the frequency of vancomycin-resistance has progressively increased all over the world, mainly in the last years (around 20% in the United States) (in Centers for Disease Control and Prevention. 2002. Morb Mortal Weekly Rep, July 5, 51(26):565-567). In Italy, from a study carried out in 2007, a frequency of vancomycin-resistance of about 2.5% in *E. faecalis* and of about 20% in the less frequent *E. faecium* was found (European Antimicrobial Resistance Surveillance System, EARSS, 2007).

In Gram-negative microorganisms, a very heterogeneous distribution of resistances is observed, with an increasing trend, mainly related to fluoroquinolone-, aminopenicillin- and aminoglicoside-resistance in *E. coli* and *K. pneumoniae/oxytoca*, and carbapenem-resistance in *P. aeruginosa* ("Antibiotic-resistance surveillance and use of systemic antibiotics in Emilia-Romagna" Dossier 173/2009, Agenzia sanitaria e sociale regionale dell'Emilia-Romagna). Recently, the increased incidence of wide range beta-lactamase-producing Gram-negative bacteria has awakened remarkable interest for the epidemiological/microbiological consequences and for the importance in therapy (from European Centre for Disease Prevention and Control (ECDC) and European Medicines Agency (EMEA). ECDC/EMEA Joint Technical Report—The bacterial challenge: time to react. Stockholm, 2009).

Also in the veterinary field there are aspects arousing a certain concern (Carattoli A et al. 2005; Busani C. et al 2004). In a report published by EFSA in 2007 (from "Trends and Sources of Zoonoses and Zoonotic Agents and Foodborne Outbreaks in the European Union in 2008", published on Apr. 26, 2010) it is stated that some among the most common zoonotic bacteria coming from animals and food in the EU, have developed antimicrobial-resistance. In particular, among the tested bacteria, ampicillin-, sulfonamide- and tetracycline-resistance was frequently observed and, in different countries, fluoroquinolone-, macrolide- or third-generation cephalosporin-resistance (important antibiotics in the treatment of human infectious diseases too) was reported (Trends and Sources of Zoonoses and Zoonotic Agents and Food-borne Outbreaks in the European Union in 2008", published the Apr. 26, 2010). Such concerns are related to the observation of high levels of fluoroquinolone-resistance in strains of *Salmonella* isolated from poultry and in strains of *Campylobacter* isolated from poultry, cattle and pigs destined to be consumed, and to the importance that some of these antibiotics have in the treatment of human infectious diseases.

Living organisms defend themselves from invasion by foreign agents through two types of responses: a so-called "innate or natural" and an "acquired or specific" immunity. Innate immunity represents a defence mechanism existing before any contact with an antigen. It makes use of different mechanical and chemical factors (integrity of epithelia, skin, saliva, gastric secretion), humoral factors (lysozime, complement, interferon), phagocytic cells (neutrophils, macrophages), dendritic cells, natural killer cells (NK) and commensal bacterial flora.

Antimicrobial peptides represent a further route for the innate response to microbial infections (Hartmann M., et al. 2010, Antimicrob. Agents Chemother. 54:3132-3142). They have double importance, in that they protect about 80% of the animal species and almost all the plants, and play a key role also in immunity of superior animals, providing a sort of first line of defence that stimulates and actively cooperates with the adaptive immune responses (Torsi A and Sandri L., Curr. Pharm. Design, 2002 8: 743-761). In superior animals, they represent the "effector" molecules of innate immunity (Boman H G., J Intern Med. 2003 254:197-215).

Antimicrobial peptides show a wide spectrum of activity: they quickly kill bacterial cells and are active against various clinically relevant antibiotic-resistant strains (Hancock and Chapple, Antimicrob Agents Chemother, 1999 43:1317-1323; Proc Natl Acad Sci USA. 2000 97:8856-886; Zasloff M., Nature, 2002 415:389-395).

It has been additionally demonstrated that, for bacteria, it is much more difficult to become resistant to proteins with antimicrobial activity, in that this would require a rearrangement or modification of the lipidic composition of their membrane, an uneconomic and "costly" process for all microbial species (Zasloff M., Nature, 2002 415:389-395).

Most antimicrobial peptides act by directly altering the membrane of target cells (Thevissen et al., Mol Plant-Microbe Interact. 2000, 13:54-61). Bacterial membranes are rich in anionic phospholipids, such as phosphatidylserine and phosphatidylglycerol: this determines an electrostatic interaction of the positively charged peptide with the membrane itself, that is the basis of the subsequent perturbation effect of the double layer.

In the case of Gram-negative bacteria, it has been seen that the peptide first interacts with the polyanionic lipopolysaccharide molecules of the external membrane, and then it is able to permeabilize it or to be captured inside. In the case of Gram-positive bacteria, instead, the peptide is probably attracted by teichoic and teichuronic acids and by other anionic groups found externally on the peptidoglycan layer. The different composition of the membranes, in fact, is the basis of the selectivity that some of these peptides have for bacterial cells.

Eukaryotic cell membranes are characterized by a high content of zwitterionic phospholipids, such as phosphatidylcholine, sphingomyelin and phosphatidylethanolamine. Additionally, they are rich in cholesterol, absent in bacteria, which seems to inhibit the action of such peptides giving membranes a certain resistance (Zasloff M., Nature, 2002 415:389-395).

Another important selectivity factor is the value of the membrane potential: a more negative potential inside the cell, typical of bacterial cells (100-150 mV), eases the interaction of the peptide with the lipidic layer (Bechinger B. J Membr Biol. 1997 156:197-211).

Two major general mechanisms have been proposed to explain the effect following interaction of the peptides with the cytoplasmic membrane:
- a "detergent" effect, where the amphipatic structure of such molecules would interact with the lipidic double layer, disrupting its organization and determining the leakage of the cytoplasmic components;
- the formation of channels, due to aggregation of peptide monomers in the lipidic double layer (Le Guerneve C et al., Archives of Biochemistry and Biophysics 1998 360:179-186) and described in the model by Shai-Matsuzaki-Huang (Zasloff M., Nature, 2002 415:389-395).

Since 1985, a number of antimicrobial peptides have been identified, reaching the remarkable number of about 600 compounds in 2010. However, most of these peptides show one or more disadvantages that limit their potential therapeutic use (Stein A. and Raoult D., Clin Infect Dis 2002 35:901-902).

For example, the antimicrobial peptide polymyxin B requires cyclization for its stabilization and biological activity. Additionally, this peptide causes nephrotoxicity, neurotoxicity and hyperthermia when used at therapeutically efficient concentrations (Ostronoff et al., Int. J. Infect. Dis, 2006 10: 339-340).

Another example is provided by Temporin L. It is an antimicrobial peptide isolated from Rana temporaria, toxic for eukaryotic cells comprising human ones (Rinaldi et al., Biochem J. 368: 91-100, 2002). Bovine Myeloid Antimicrobial Peptides (BMAPs) have shown toxicity against cultured endothelial cells and, generally, against almost all the cell lines of the haematopoietic line (Risso et al., Cell Immunol., 189: 107-115, 1998). Similarly, also Bombinin H2, isolated from the anuran Bombina orientalis, determines marked haemolysis (Csordas A. and Michl H.; Monatsh Chem 101: 182-189, 1970).

It is therefore necessary to identify those antimicrobial peptides that have high biological activity against microorganisms, associated with weak or null toxicity against eukaryotic cells, wide spectrum of activity and high structural stability for different clinical applications.

Additionally, it has been observed that many peptides with proven antibacterial in vitro, once tested in other culture media in vitro, or in vivo, lose such antibacterial activity or most of it; such phenomenon has been attributed to the inactivating action on peptides by high salt concentrations, such as those present in different compartments of the human body or in some culture media. Hence, it would be further useful to have groups or subgroups of peptides that, in addition to a useful basal antimicrobial activity, retained the same also in the presence of high salt concentrations, so as to obtain a consistent antibacterial effect in vivo in all the physiological compartments, including those containing high amounts of salts.

SUMMARY

In response to the drawbacks showed by antibiotics currently on the market or available for the treatment of antibiotic-resistant infections, an object of the present invention is a series of cyclic cationic peptides with antimicrobial activity and wide spectrum of activity.

The peptides of the invention have a length of 15 to 21 amino acids, are cyclizable via formation of a disulfide bridge between two amino acids containing sulphur, properly located in proximity to the —$NH_2$ terminal and —COOH terminal regions, taking a cross beta sheet structure in their cyclized form. Furthermore, the central portion of the peptide is characterized by the presence of a number of charged amino acids, partly or completely alternating with neutral amino acids. More specifically, peptides show a sequence of A-B-C-D-C'-B'-A' type, where: units A and A' represent the —$NH_2$ terminal and —COOH terminal regions respectively; units B and B' consist of amino acids containing sulphur; units C consist of 5 amino acids selected from: (a) hydrophobic amino acids and (b) basic amino acids or amino acids forming hydrogen bonds; unit D consists of glycine and one basic amino acid. The substructure C-D-C' is characterized in that it contains 5 to 9 points of alternation between amino acids of group (a) and group (b), or vice versa.

The peptides object of the present invention show significant antibacterial activity. The hairpin loop structure of the peptide, guaranteed by the group D in the central portion of the sequence, juxtaposes the two B amino acids containing sulphur that, in a suitable environment (air or oxidizing conditions), form a disulfide bridge. Cyclization of the structure contributes to the stability of the peptide and the resistance against the action of bacterial peptidases. The above-cited sequence comprises a percentage of hydrophobic amino acids, so as not to perturb the membranes of the eukaryotic cells, guaranteeing weak/null toxicity for such cells. Furthermore, the disposition of hydrophobic amino acids in discrete regions, separated from charged amino acids, that is basic and/or hydrogen bond-forming, gives the peptides higher efficacy, and possibly also higher salt-insensitivity. Such peptides, eventually, show high solubility in aqueous solvents.

The invention also relates to the use of said peptides in the treatment of infections concerning different districts (for example, pulmonary, gastrointestinal, urinary), cutaneous infections and medical/surgical diseases complicated by bacterial or fungal superinfections.

The peptides object of the present invention are readily synthesized, highly efficient, proteolytically stable, essentially salt-insensitive, not haemolytic and not cytotoxic for eukaryotic cells.

The antibacterial spectrum of the antimicrobial peptides of the present invention includes Gram-negative and Gram-positive microorganisms. Gram-negative microorganisms are, for example, *Escherichia coli* ATCC 25922, *Pseudomonas aeruginosa* ATCC 27853 and *Stenotrophomonas maltophilia* ATCC 13637: in particular, $LD_{90}$ against *E. coli* between 0.83 µM (1.5 µg/ml) and 10.64 µM (19.63 µg/ml) and for *P. aeruginosa* between 0.87 µM (1.59 µg/ml) and 7.68 µM (16.29 µg/ml) were observed; $LD_{90}$s obtained against *Stenotrophomonas maltophilia* range between 1.88 µM (3.42 µg/ml) and 2.67 µM. Of particular interest are also the results obtained against Gram-positive bacteria, as highlighted by the activity against strains of meticillin-resistant *S. aureus* (MRSA ATCC 43300). For the tested peptides $LD_{90}$s range between 0.85 µM (1.65 µg/ml) and 0.90 µM (1.72 µg/ml). Equally interesting are the results obtained against strains of meticillin-sensitive *S. aureus* (ATCC 25923), with $LD_{90}$ comprised between 1.42 µM (2.89 µg/ml) and 13.4 µM (28.77 µg/ml). The peptides of the present invention demonstrated to be efficient also against fungal and yeast species, as highlighted by the activity against *Candida albicans* ATCC 10231 and *Malassezia pachydermatis* ATCC 14522; values of $LD_{90}$ obtained with different peptides for both tested species were comprised between a minimum value of 0.68 µM (1.24 µg/ml) and a maximum value of 39 µM (about 70 µg/ml).

Said peptides can be effectively used as primary agents or as adjuvants in the treatment of infectious diseases concerning different body districts, both in humans and animals. Furthermore, the peptides object of the invention can also be employed in the treatment of infections of vegetal organisms.

DETAILED DESCRIPTION

The term "peptide", within the present invention, is defined as a multiplicity of amino acid residues linked by peptide bonds. It has the same meaning of polypeptide and protein and can be used interchangeably. Amino acids forming a polypeptide are herein regardlessly identified by their complete name, or by their respective international official abbreviations (1- or 3-letter code).

The term "series", in the present document, is defined as all the possible variants of the peptide of the invention, wherein one or more amino acids of the peptide sequence are substituted by a homologous amino acid so that the properties of the peptides are retained, even if not necessarily at the same level. Another variant can show higher or lower activity and/or a wider spectrum (for example, activity against a wider range of microbes), or be more specific for a particular microorganism. Preferably, conservative substitutions of amino acids are carried out in one or more amino acid residues.

Figure 1:
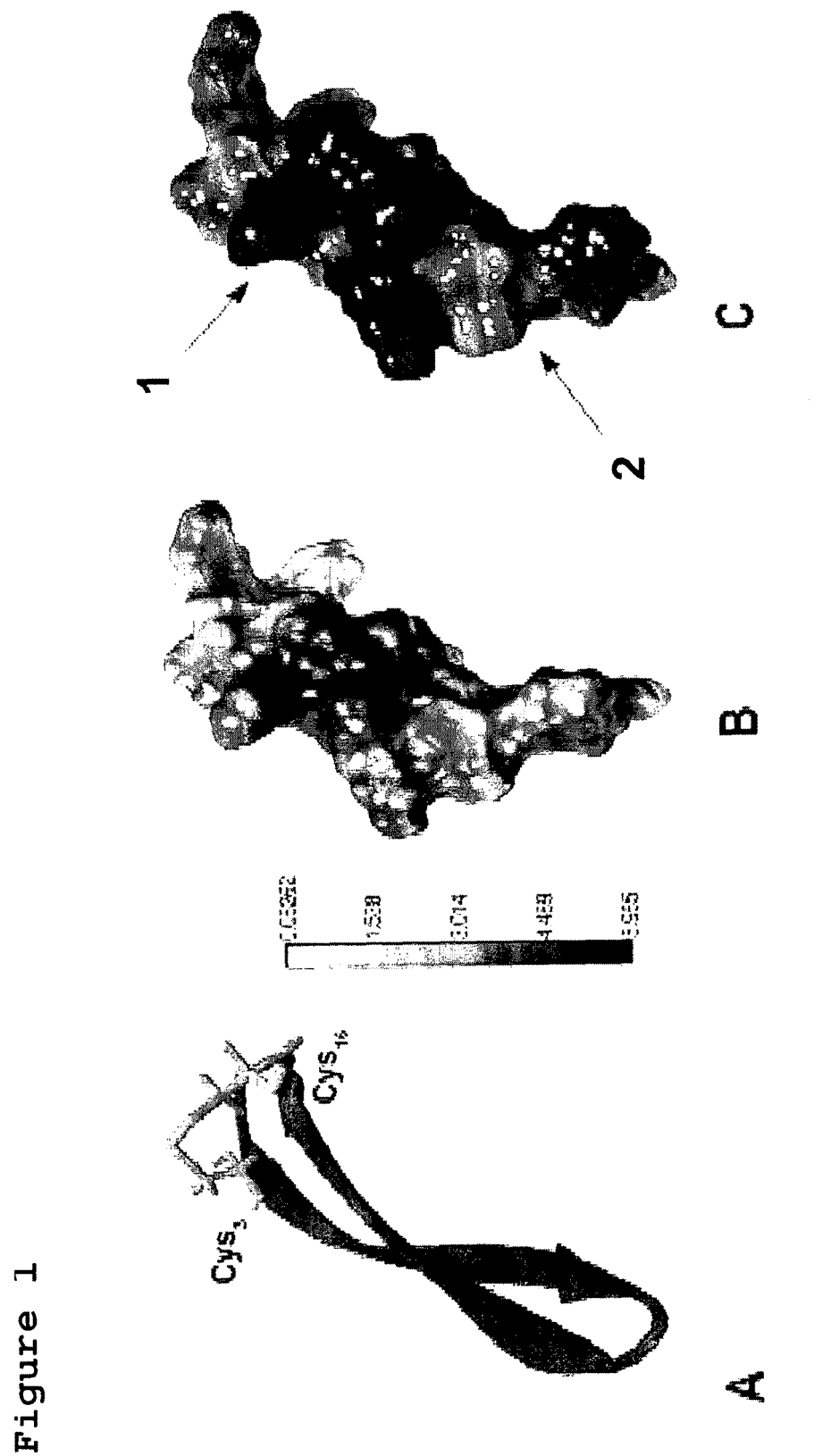
FIG. 1: Schematic representation of the structure of the peptides. A: evidence of the disulfide bond; B: electrostatic potential; C: (1)=charged area; (2)=hydrophobic area.

The term "beta sheet" is referred to the three-dimensional structure of the cyclized peptide as illustrated e.g. in FIG. 1; there, the organization of the beta sheet peptide can be observed, where each strain displays a right-hand torsion (twist) of about 30°; such geometry represents the compromise between conformational energy optimization of the two strains forming the sheet, and maintenance of the geometry of the intra-strain hydrogen bonds. In the above cited sequence, units A, B, C, D, C', B', A' are linked in the order A-B-C-D-C'-B'-A' to form a linear sequence; such sequence is cyclizable or cyclized by direct bonding between the two units B. In said structure, the units named with the same letter are not necessarily the same, but can contain different amino acids; consequently, considering the central group D, the invention includes both symmetric peptides and asymmetric ones.

Units A represent the terminal regions of the peptide: unit A refers to the —NH$_2$ terminal region, while unit A' refers to the —COOH terminal region. Each unit A and A' consists independently of 1, 2 or 3 amino acids; the type of these amino acids is not determining, however they can be preferably selected from histidine, lysine, glycine, tryptophan, alanine, valine; also preferably, the total number of amino acids present in these two units A and A' is equal to 3, that is 2+1 or 1+2.

Units B are represented by an amino acid containing sulphur, in particular cysteine or methionine. Units B are involved in the formation of the disulfide bridge responsible for cyclization of the peptide. Cyclization can be achieved at the time of peptide synthesis, or it can occur subsequently in the presence of a suitable amount of environmental oxygen. The invention includes synthesis, formulation and therapeutic use of the peptide both in straight form and in cyclized form.

Unit D is represented by glycine and a basic amino acid, preferably with the sequence: basic amino acid→glycine, in A→A' direction; here, the basic amino acid is preferably arginine. The glycine present in D, suitably supported by arginine, allows the hairpin loop structure of the peptide and, in association with the units C linked to it, a suitable distance between the units B forming the disulfide bridge.

Units C, independently, consist of 5 amino acids selected:
a) both in the group of hydrophobic amino acids,
b) and in the group of basic or hydrogen bonds-forming amino acids.

Hydrophobic amino acids of group (a) are selected from: alanine, phenylalanine, isoleucine, leucine, proline, tyrosine, tryptophan and valine. With reference to the overall number of all the amino acids of the peptide, they preferably represent between 30 and 50%, more preferably between 35 and 45%, e.g. between 39 and 43%.

Basic amino acids of group (b) are selected from: lysine, histidine, arginine.

Amino acids forming hydrogen bonds of group (b) are selected from asparagine, glutamine, serine, threonine.

In the present invention, it is essential that each unit C contains both amino acids of group (a) and amino acids of group (b); as members of group (b), it is possible to use freely basic amino acids, amino acids forming hydrogen bonds, or both. In a preferred variant, the units C contain, mainly or totally, basic amino acids as members of group (b).

A fundamental characteristic of units C is the high degree of alternance between positively charged amino acids of group (b), and electrically neutral amino acids of group (a). In particular, the sequence C-D-C' contains 5 to 9 points of alternation between: (a) hydrophobic amino acid and (b) basic or hydrogen bond-forming amino acid, or vice versa. The number of "points of alternation" equals the number of peptide bonds that, in the sequence C-D-C', separate an amino acid of group (a) from an amino acid of group (b) directly linked to it: for example the sequence Ala-His-Ala-Thr-Phe contains 4 points of alternation, corresponding to the 4 peptide bonds found in the sequence; on the other side, a sequence Lys-Ala-Phe-Lys-Phe contains only 3 points of alternation: because Ala and Phe belong to the same class (a), and then the Ala-Phe bond does not count as a "point of alternation". For the purposes of the present invention, "points of alternation" also include the bond between the basic amino acid present in D and the amino acid of unit C bound to it, in case said amino acid is a hydrophobic amino acid; vice versa, the bonds involving glycine and amino acids containing sulphur, do not count as "points of alternation", regardless of the amino acid bound to them.

Hence, in units C amino acids of type (a) and (b) are typically alternate between them; however, this does not exclude the possibility of limited contiguities between amino acids of the same group ((a) or (b)), provided that said number of points of alternation in the sequence C-D-C is fulfilled.

The alternation of charge achieved in the substructure C-D-C is advantageous for the general antibacterial activity of the peptide.

A preferred subgroup of peptides belonging to the family described above is that containing a total of 17 amino acids, wherein units A and A' consist independently of 1 or 2 amino acids, units B and B' are both Cys, at least one of units C and C' includes Lys, all the amino acids at positions 6, 8, 13 (numbered from A to A') belong to said group (i) of hydrophobic amino acids, and amino acids at positions 9 and 10 are Arg and Gly.

A more preferred subgroup is characterized in that it contains, in addition to the previously listed characteristics, a hydrophobic amino acid especially at position 11 (always numbering from A to A'). Such characteristic has proven particularly useful in increasing the salt-insensitivity of the peptide, that is the maintenance of its antibacterial action even in the presence of high concentrations of salt. This property is of particular importance, in that the membranolytic activity of the antimicrobial peptides is generally based on the electrostatic interaction with negatively charged bacterial or fungal membranes; normally, the presence of free ions (e.g. Na$^+$, Cl$^-$, usually present in the assay medium or in physiological/pathological fluids) masks the negative charge present on the bacterial membrane, reducing the binding efficiency of the peptide and then the efficacy of the treatment. The present peptides are not influenced by this undesired phenomenon, retaining a significant efficacy (especially against Gram-negative bacteria) in the presence of high environmental ion concentrations.

All the amino acids present in the present peptide can be regardlessly present in D- or L-form; preferably, they are mainly (that is over 50%) or totally in the L-form.

Another preferred aspect of the invention relates to peptides constituted of at least 80%, for example 90%, or more preferably 91-100%, for example 100%, of L-amino acids.

Another preferred aspect of the invention relates to peptides constituted of at least 80%, for example 90%, or more preferably 91-100%, for example 100%, of D-amino acids.

All the amino acids can be used in their natural state or in the form of their synthetic derivatives.

A preferred group of peptides is that where:
unit A (NH$_2$— terminal) contains 2 amino acids, and unit A' (COOH— terminal) contains 1 amino acid,
units B and B' are both represented by cysteine.

Specific preferred peptides according to the present invention are the peptide identified as AMP2041 (SEQ.ID.No.:1), the peptide identified as AMP72 (SEQ.ID.No.:2), and the peptide identified as AMP126 (SEQ.ID.No.:3). Further peptides useful for the purposes of the invention are those having the sequences SEQ.ID.No.: 4-54 as described herein.

Equally preferred are the close homologues of each of said SEQ.ID.No.: 4-54, characterized in that they are modified for only one amino acid at any position between no. 1 and 17, where said modification does not involve amino acids at positions 3, 9, 10, 16; the modification consists in substituting said amino acid with another amino acid selected from the 20 natural amino acids; preferably, the amino acid is substituted with another amino acid belonging to the same category, (a) or (b) as defined above: for example, Ala is substituted with Leu; or Ser is substituted with Lys or Thr, etc.

The present invention includes a process for the synthesis of said peptides having the structure A-B-C-D-C'-B'-A' defined above.

Collectively, or individually, the peptides of the invention are generally synthetic peptides synthesized in vitro using chemical methods known in the art. For example, they are prepared using synthetic solid phase, liquid phase, peptide condensation procedures, or any combination of the above-mentioned techniques. Amino acids composing the peptides of the invention can be natural or synthetic. Amino acids used for peptide synthesis can be amino acids wherein the a-amino-terminal is protected by the acid-labile group N-α-t-butyloxycarbonyl (Boc) according to the work of Merrifield (J. Am. Chem. Soc., 85: 2149-2154, 1963) or by the base-labile 9-fluorenylmethoxycarbonyl (Fmoc) as described by Carpino and Han (J. Org. Chem., 37: 3403-3409, 1972). Both Boc- or Fmoc-protected amino acids can be obtained from different commercial sources, such as, for example, Fluka, Sigma-Aldrich Bachem, Advanced Chemtech, Cambridge Biochemical Research.

In general, solid phase methods of chemical synthesis, according to M. Bodansky, Principles of peptide synthesis, (Springer-Verlag, Berlin, 1984) or J M Stewart and J D Young, Solid Phase Peptide Synthesis (Pierce Chemical Co., Rockford, Ill. 1984), consist in sequential addition of one or more amino acids to the growing peptide chain. Generally, the amine or carboxyl group of the first amino acid is protected by an optimal protecting group. The first protected amino acid is attached to a solid inert support, for example a resin. The protecting group is then removed from the residue bound to the resin and the next (properly protected) amino acids are sequentially added. After reaching the number of amino acids, all the remaining protecting groups (and any solid support) are sequentially or simultaneously removed, to give the final peptide.

It is possible to add more than one amino acid at a time to the growing chain, for example, by coupling (in suitable experimental conditions avoiding the formation of racemates due to the presence of chiral centres) a protected tripeptide with a properly protected dipeptide to form, after deprotection, a pentapeptide as described, for example, by Merrifield in G. Barany and R B Merrifield, Peptides: analysis, synthesis, biology, E. and J. Gross Meienhofer eds., vol. 2 (Academic Press, New York, 1980, pp. 3-254).

Said peptides can be synthesized by firms providing the service of synthesis of custom peptides, for example, but not limited to, Sigma-Aldrich (St. Louis, Mo., USA), Selleck-Chem (Houston, Tex., USA), Invitrogen (Grand Island, N.Y., USA), Abgent (Oxfordshire, OX144RY, United Kingdom).

The degree of purity of the peptide compound can be determined by various methods, among which by identification of HPLC peaks. Preferably, a peptide producing a single peak of height and width equal to at least 75% of the input material on an HPLC column is preferred. Even more preferred is a peptide producing a single peak that is at least 87%, at least 90%, at least 99% or even 99.5% of the input material on an HPLC column.

To guarantee that the peptide obtained using one of the abovementioned synthetic techniques is the desired peptide for the uses or formulations described hereinafter in the present invention, analysis of the composition of the peptide is carried out with the aid of different analytical methods known in the art. The analysis of the composition can be carried out, for example, using high resolution mass spectrometry to determine the molecular weight of the peptide. Alternatively, the content of amino acids of a peptide can be confirmed hydrolyzing the peptide in acid solution to identify and quantify the components of the mixture using HPLC, or an amino acid analyzer. Equally useful are thin layer chromatography methods, they can also be used to identify one or more constituent groups or residues of a desired peptide.

Another preferential, but not limiting, aspect of the peptides of the invention relates to the polar angle comprised between 90° and 180°, preferably between 91° and 179°, more preferably between 104° and 115°. The term "polar angle" in the present document means the measure of the angle formed between the polar and non-polar sides of a peptide formed in an amphipatic structure.

Another preferential, but not limiting, aspect of the peptides of the invention relates to the Boman index comprised between −1 and +4. Preferably between −0.5 and +3 and even more preferably between +1 and +2.5, for example between +1.1 and +2.0. The term "Boman index" in the present invention means the sum of the energies for the transfer from water to cyclohexane of the lateral chains of the single amino acids composing the peptides, divided by the total number of residues, according to what described by Radzeka and Wolfenden (1988) in "Comparing the polarities of amino acids: side-chain distribution coefficients between vapour phase, cyclohexane, 1-octanol and neutral aqueous solution." (Biochemistry 27:1664-1670). Calculated values are negative but the sign (+ or −) is the opposite.

Another preferential, but not limiting, aspect of the invention relates to the percentage of water solubility of the peptides of the invention, comprised between 40% and 90%, preferably between 91% and 97%, even more preferably between 97.5% and 100%, for example 98%. The estimated percentage of solubility is calculated by the two-parameter solubility model of Wilkinson-Harris as described in Wilkinson D L and Harrison R G (1991) Bio/Technology 9, 443-448.

Collectively or individually, the peptides of the invention are provided with biological activity towards biota (cellular organisms belonging to the domains Archea, Bacteria or Eukaryota).

A preferential aspect of the peptides of the invention relates to the lack of biological activity towards biota belonging to the domain Eukaryota, preferably biota belonging to the subkingdom Eumetazoa, even more preferably biota belonging to the phylum Chordata.

Collectively or individually, the peptides of the invention are provided with antimicrobial activity for a wide range of pathogens such as, for example, bacteria, fungi, yeasts, parasites, protozoa and viruses. A "pathogenic agent" is generally defined as any (uni- or multi-cellular, or having subcellular organization) organism causing a disease in an organism.

Collectively or individually, the antimicrobial peptides of the invention are readily synthesized, highly efficient, proteolytically stable, essentially salt-insensitive, not haemolytic and not cytotoxic.

The mass of the peptides of the invention can be determined through procedures known in the art, for example, mass spectroscopy. Essentially, this technique includes ionization of a compound and subsequent separation of the ions produced based on their own mass/charge ratio. Mass spectrometers have different methods to determine the mass/charge ratio of the ion, for example the time of flight. Essentially, ions coming from the source are accelerated by a potential (V) to the same kinetic energy, then are allowed to fly along a tube towards a detector. If one spectrometer has a flight tube of a length L, the time of flight for a given ion is given by: $t=(L^2*m/2*z*e*V)$. Starting from the m/z ratio, function of the residence time in the flight tube, the mass of a given ion can be calculated. The flight tube, though, has low resolution (low ability to discriminate two ions with similar m/z), to overcome this, most of these analyzers are provided with a "Reflectron" i.e. one mirror able to reflect ions and then to make the ion cover twice the path. In this way, it is possible to discriminate between 2 ions having very similar times of flight in the flight tube. The use of the "Reflectron" narrows the range of molecular mass that can be analyzed, that is comprised between 200 and 5000-10000 Da.

The secondary structure of peptides in solution can be analyzed by a technique known in the art, called circular dichroism. It is part of the chiroptical spectroscopies, that is those spectroscopic techniques that, using polarized light, emphasize the optical, activity of test molecules. Results obtained by this technique provide information on the percentages of secondary structures present in polypeptides. Although it is not possible to establish the position in the sequence, this technique can be used for a first screening for the choice of the solvent system for NMR analysis and as a check of the results obtained from computational calculation.

The antimicrobial activity of a peptide can be determined using a method known in the art, for example, the broth-dilution method. Essentially, this method involves the growth of a microorganism in a liquid medium until it reaches the logarithmic phase. The test peptide is serially diluted with growth medium for the test bacterium in the wells of a multiwell plate. An optimal concentration of the microorganism is added to the wells containing the serially diluted peptide. The plate is incubated in a thermostat at a temperature of 37° C. for a time sufficient for the microorganism to grow. The growth of the microorganism, evaluated in comparison with a negative control (microorganism grown in the absence of the peptide), is determined by detecting the absorbance of the solution containing the bacterium, for example, at 605 nm.

Another method known in the art to determine the antimicrobial activity of a peptide of the invention is the diffusion test in agar. Essentially, the test is carried out on agar in 14 cm or 9 cm plates. To perform the inoculum of bacteria on agar, 4-5 colonies cultured on primary isolation medium are suspended in 4-5 ml of Tryptic Soy Broth (enrichment broth), incubated for 2-6 hours until the liquid culture has reached an opacity corresponding to a value of 0.5 on the McFarland nephelometric scale (that is $1.5 \times 10^6$ bacteria). The bacterium which sensitivity is to be assayed is seeded on the agar surface. Subsequently, on the perfectly dry agar surface, discs soaked with peptide are deposed using sterile tweezers and, after making the discs adhere to the surface, the plate is incubated in a thermostat at a temperature of 37° C. for 24 hours. The diameter of the inhibition zones allows to define which bacterium is resistant, has intermediate resistance or is sensitive to the peptide.

A further method to determine if a peptide has antimicrobial activity consists in verifying the existence of a damage to the bacterial membrane. This method essentially consists in contacting, in a liquid medium, the microorganism with a peptide. To the liquid medium, a molecule able to cross the intact membrane of the microorganism is added. Once entered, inside the microorganism, it is digested to form a product that is no longer able to cross the membrane. The medium in which the microorganism is dispersed, is analyzed for the presence of said product. The presence of such product in the medium in which the microorganism is incubated is an index of damage to the membrane caused by the peptide and is an index of antimicrobial activity of the peptide. An example of a suitable molecule is calcein AM. Calcein AM is converted into free calcein inside the microorganism. Normally, free calcein is not able to cross the cell membrane of the microorganism and to be present in the culture medium. Then, the detection of free calcein in the medium is an index of damage to the cell membrane of the microorganism, and then of antimicrobial activity of the peptide.

Another method useful to identify a damage to the bacterial membrane exploits the ability of β-galactosidase to convert the chromogenic artificial substrate ortho-nitrophenyl-β-D-galactopyranoside (ONPG) into glucose and o-nitrophenol. This method first described by Jeffrey Miller in 1972 and published in "Experiments in Molecular Genetics" was subsequently modified by Zhang and Bremer in 1995 (The Journal of Biological Chemistry, 1995, 270, 11181-11189). Essentially, this method consists in mixing in a proper liquid medium an aliquot of bacterial cells and a permeabilizing agent, for example detergents such as Triton-X100 or Tween20, or the peptides of the invention, that destroy bacterial membranes leaving the enzyme β-galactosidase intact. After a proper incubation period, a solution of ONPG is added into the culture medium. The β-galactosidase released by damaged bacteria metabolizes ONPG, releasing free nitrophenol. Nitrophenol, that gives the medium a yellow colour, is quantified by spectrometric analysis at 405 nm.

In the present invention, cytotoxicity of the peptides was also determined, for example, by determining haemolysis of red blood cells and scoring the antimicrobial peptides based on their minimum haemolytic concentration. In the present document, MHC10 is defined as the concentration of peptide that determines 10% of haemolysis, MHC50 is the concentration of peptide that determines 50% of haemolysis and MHC90 is the concentration of peptide that determines 90% of haemolysis. Peptides that at the concentration of 100 μg/ml fell in the class defined as MHC10 were selected.

In the present invention, cytotoxicity of the peptides against a cell line of T lymphocytes was also determined, for example, Jurkat cells. Cells were cultured in the presence and in the absence of peptides and the damage to the membrane was evaluated by the vital stain Trypan Blue.

A preferred aspect of the invention relates to the use of a peptide having the A-B-C-D-C'-B'-A' structure defined above, for manufacturing a medicament useful for the treatment of a subject affected by an infection caused by bacteria, fungi and/or yeasts; the invention additionally comprises the same peptide for use in the treatment of a subject affected by an infection caused by bacteria, fungi and/or yeasts. In a first variant, the treatment is particularly directed against the group of Gram-negative bacteria; in a second variant, the treatment is directed against the group of Gram-positive bacteria; in a third variant, the treatment is directed against the group of fungi and yeasts; in a fourth variant, the treatment is directed against microorganisms belonging to more than one of said groups. The term "treatment" refers to the effects of the peptides of the invention able to provide benefit to patients affected by an infectious disease, for example an improvement of the conditions of the patient or a delay in the progression of the disease. In the present document, term "infection", or its synonym "infectious disease" means the invasion, colonization and/or multiplication of a microorganism inside or on another host organism. The term "microbial infection" means an infectious disease caused by a pathogenic agent, as previously defined, for example, a bacterium, a parasite, a protozoan, a virus or a fungus, comprising yeasts. In the present document, the term "subject" defines any multicellular organism, among which a human being, animal, plant or insect that can be infected by a microorganism. Preferably, the subject is any animal organism, for example a human being or an animal, that can be infected by a microorganism against which an antimicrobial peptide or a variant thereof is active.

A pathogenic bacterium, as previously defined, can originate from one of the bacterial species selected in the group including: *Staphylococcus* spp., for example, *Staphylococcus aureus* (e.g. *Staphylococcus aureus* ATCC 25923), *Enterococcus* spp., for example, *Enterococcus faecalis* ATCC 29212; *Pseudomonas* spp., for example *Pseudomonas aeruginosa* ATCC 27853; *Mycobacterium* spp., for example *Mycobacterium tuberculosis; Enterobacter* spp.; *Campylobacter* spp.; *Salmonella* spp. (e.g. *Salmonella enteritidis* ATCC 13076); *Streptococcus* spp., for example *Streptococcus* group A or B, *Streptococcus pneumoniae, Helicobacter* spp., for example *Helicobacter pylori; Neisseria* spp., for example *Neisseria gonorrhea, Neisseria meningitidis; Borrelia burgdorferi, Shigella* spp., for example, *Shigella flexneri; Escherichia coli* (ATCC 25922); *Haemophilus* spp., for example *Haemophilus influenzae; Francisella tularensis, Bacillus* spp., for example *Bacillus anthracis; Clostridium* spp., *Clostridium botulinum, Yersinia* spp., for example, *Yersinia pestis; Treponema* spp.; *Burkholderia* spp.; for example *Burkholderia cepacia* ATCC 17759, *B. mallei* and *B. pseudomallei; Stenotrophomonas* spp., for example *Stenotrophomonas maltophilia* ATCC 13637.

The biological activity of the peptides of the invention against microorganisms was determined, for example, through broth-microdilution assay and count of the colonies in a plate. In the present invention, the ability of the peptides to reduce or prevent the growth of those bacteria involved in primarily clinically relevant infectious diseases was determined. For example, the activity on Gram-negative bacteria was verified with reference to bacteria such as *Pseudomonas aeruginosa, Escherichia coli, Stenotrophomonas maltophilia, Burkholderia cepacia*. In particular, *Pseudomonas aeruginosa* is a problematic Gram-negative bacterium by virtue of its invasivity and heterogeneous resistance to antibacterial chemotherapies. This microorganism is responsible of severe infections and is the cause of severe morbidity in immunocompromised subjects due to viral infections such as HIV, anticancer chemotherapy or immunosuppressive therapies. Additionally, this bacterium is often the aetiological agent of severe infectious diseases of lower respiratory tract, urinary tract, cutaneous lesions (wounds, ulcers) in in-house juvenile population, including subjects affected from cystic fibrosis, and hospitalized patients. In the last years, the incidence of infections by *Pseudomonas*, in cystic fibrosis, has been dramatically increasing.

*Escherichia coli* is a Gram-negative microorganism belonging to the family of Enterobacteriaceae, to which bacteria such as *Shigella, Salmonella, Klebsiella* or *Proteus* belong. *Escherichia coli* is an important pathogenic agent often causing infectious diseases of the urinary tract, bacteremias, hospital and community acquired pneumonia and various infectious diseases of the abdominal cavity. The emerging resistance to antibacterial chemotherapies observed in the last years in *Escherichia coli* is becoming a serious health problem. Of particular interest is the resistance related to the production of wide spectrum beta-lactamases that has made this bacterium resistant to cephalosporins and fluoroquinolones, in particular to ciprofloxacin.

*Stenotrophomonas maltophilia* is an aerobic Gram-negative bacillus widely distributed in different natural habitats, animals or humans. Currently, it is believed to be responsible of hospital acquired infectious diseases such as bacteremias, meningitis, eye infections, pneumonia, infections of the urinary tract, infections of soft tissues and skin. Infectious diseases caused by this microorganism are generally considered a risk factor in all those diseases in which a reduction of the immune response is observed, for example, in neoplasias, chronic respiratory diseases, such as cystic fibrosis or chronic obstructive pulmonary diseases, and it is considered to be the agent responsible of infectious endocardites. These generally hospital-acquired endocardites are related to the contamination of catheters and are often fatal due to the intrinsic resistance of this bacterium to common antibiotics.

The activity on Gram-positive bacteria was verified with reference to bacteria such as *Staphylococcus aureus* and its meticillin-resistant variant.

A fungal pathogen can originate from one of the fungi (comprising yeasts) belonging to the group including genera *Candida* spp. (for example *C. albicans*), *Epidermophyton* spp. *Exophiala* spp., *Microsporum* spp., *Trichophyton* spp. (for example *T. rubrum* and *T. interdigitale*), *Tinea* spp., *Aspergillus* spp., *Blastomyces* spp., *Blastoschizomyces* spp., *Coccidioides* spp., *Cryptococcus* spp. (for example *Cryptococcus neoformans*), *Histoplasma* spp., *Paracoccidiomyces* spp., *Sporotrix* spp., *Absidia* spp., *Cladophialophora* spp., *Fonsecaea* spp., *Phialophora* spp., *Lacazia* spp., *Arthrographis* spp., *Acremonium* spp., *Actinomadura* spp., *Apophysomyces* spp., *Emmonsia* spp., *Basidiobolus* spp., *Beauveria* spp., *Chrysosporium* spp., *Conidiobolus* spp., *Cunninghamella* spp., *Fusarium* spp., *Geotrichum* spp., *Graphium* spp., *Leptosphaeria* spp., *Malassezia* spp. (for example *Malassezia furfur*), *Mucor* spp., *Neotestudina* spp., *Nocardia* spp., *Nocardiopsis* spp., *Paecilomyces* spp., *Phoma* spp., *Piedraia* spp., *Pneumocystis* spp., *Pseudallescheria* spp., *Pyrenochaeta* spp., *Rhizomucor* spp., *Rhizopus* spp., *Rhodotorula* spp., *Saccharomyces* spp., *Scedosporium* spp., *Scopulariopsis* spp., *Sporobolomyces* spp., *Syncephalastrum* spp., *Trichoderma* spp., *Trichosporon* spp., *Ulocladium* spp., *Ustilago* spp., *Verticillium* spp., *Wangiella* spp.

The biological activity of peptides of the invention against a fungus or a yeast was determined for example, by broth-microdilution assay and count of the colonies in a plate. For example, the ability of an isolated peptide or of one belonging to a library of peptides to inhibit the growth and/or kill fungi (comprising yeasts) belonging to the genus *Candida* spp. or *Malassezia* spp., for example, *Candida albicans* or *Malassezia furfur*, was determined.

*Malassezia*, previously known as *Pityrosporum*, is a genus of fungi living on the skin of various animals, including humans, and occasionally causing opportunistic infections. Recently, thanks to the use of molecular biology techniques, it was observed that this fungus is the pathogenic agent of a number of dermatitis in humans, including dandruff and seborrhoeic dermatitis (Sugita T, Tajima M, Takashima M, et al., 2004, "A new yeast, *Malassezia*

*yamatoensis*, isolated from a patient with seborrhoeic dermatitis, and its distribution in patients and healthy subjects", Microbiol. Immunol. 48 (8): 579-83). Additionally, it was discovered that cutaneous rashes observed in pityriasis versicolor are due to infection by this fungus (Guillot J, Hadina S, Guého E, 2008, "The genus *Malassezia*: old facts and new concepts". Parassitologia 50 (1-2): 77-9). The members of the genus *Malassezia* spp., in particular *Malassezia pachidermatis*, are of particular importance in the field of veterinary medicine. It develops as a saprophyte on the skin and in the external ear canal of dogs and cats, in addition to other mammals. It is strictly host-adapted, so much as it is not found free in nature. It is an opportunistic fungus expressing its pathogenic power only in the presence of promoting factors: excessive humidity, increased secretion of earwax or sebum, skin folds. It comprises one of the most frequent agents of external otitis in the dog. Topical therapy seems to be the most indicated in the management of ear infections by *Malassezia* spp., where there is a need for multivalent products having simultaneously fungicidal/bactericidal activity.

In a preferred, but not limiting, variant the treatment is directed against a microorganism selected in the group of *Pseudomonas* spp., *Escherichia* spp., *Stenotrophomonas* spp., *Burkholderia* spp., *Candida* spp., or *Malassezia* spp.

Collectively, or individually, the peptides of the present invention can be useful also in the treatment of infections generally associated with the skin among which, and not limited to, ulcers and lesions, skin wounds, cuts or burns.

A further preferred aspect of the invention reports that the peptides, collectively or individually, are useful in the treatment of bacterial cutaneous infections or pyodermites.

Another aspect includes the collective or individual use of the peptides of the invention in the treatment of (clinical or surgical) diseases complicated by bacterial superinfections among which, and not limited to, infections associated to mucosae, infections associated to gastrointestinal, urogenital tract, infections of the urinary tract (for example pyelonephritis, cystitis, urethritis) or respiratory infections, for example, cystic fibrosis.

Mammals, birds and, in general, other animals can be treated with the peptides described in the present invention. Mammals and birds comprise, but they are not limited to, humans, dogs, cats and bird pets and productive livestock, such as horses, cattle, sheep, goats, pigs, chicken and turkeys and poultry.

A second preferred aspect includes the use of the peptides of the invention in the treatment of infectious diseases: infections by *Klebsiella, Salmonella, Yersinia, Proteus* and *Colibacilli* of pet animals and production livestock.

Another preferred aspect relates to the treatment of glanders in equids and melioidosis in carnivores and infections by *Pseudomonas aeruginosa* in pet animals and production livestock.

A further aspect relates to the treatment of infections by *Bordetella* spp., in pet animals and production livestock; infections by *Moraxella* spp.; infections by *Francisella* spp., infections by *Brucella* spp., infections by *Campylobacter* spp., infections by *Pasteurella* spp.; infections by *Actinobacillus* spp. (actinobacillosis); infections by *Haemophilus* spp.; infections by *Streptococcus* spp. (among which mastitis in cows, strangles); infections by *Staphylococcus* spp. (among which mastitis, pyodermitis, endometritis); infections by *Bacillus* spp., among which anthrax; infections by *Clostridium* spp., among which tetanus, botulism and symptomatic anthrax; infections by *Listeria* spp. (listeriosis); infections by *Erysipelothrix* spp., among which erysipeloid; infections by *Leptospira* spp., *Serpulina* (superficial necrotic enteritis), *Treponema* spp. (sifilis of the rabbit), *Borrelia* spp. in pet animals and production livestock.

Eventually, also plants can be treated with the peptides of the invention.

Different pharmaceutical formulations containing, collectively or individually, the peptides of the invention can be prepared by procedures described in the art and with known and readily available excipients. Such formulations are part of the present invention.

In the present document, the term "excipient" means a compound or a mixture thereof optimal for use in a formulation destined to the treatment of a specific infectious disease or conditions associated with it. For example, an excipient for use in a pharmaceutical formulation, generally, should not cause an adverse response in a subject. The excipient, as previously described, should not significantly inhibit the relevant biological activity of the active compound. For example, an excipient does not significantly inhibit the antimicrobial activity of an antimicrobial peptide of the present invention or a variant thereof. An excipient can simply provide a buffering activity to keep the active compound at a pH suitable to exert its biological activity, for example, saline phosphate buffer. Alternatively or in addition, the excipient can comprise a compound, for example a protease inhibitor, that increases the activity or half-life of the peptide. In another example, the excipient can include or be itself an additional antimicrobial molecule and/or an anti-inflammatory molecule.

Collectively, or individually, the peptides of the invention can also be formulated as solutions for oral administration or as solutions suitable for parenteral administration, such as, for example by intramuscular, subcutaneous, intraperitoneal or intravenous route.

The pharmaceutical formulations of the peptides of the invention can also be in the form of an aqueous solution, a dry form or a dispersion, or alternatively in the form of an emulsion, a suspension, a cream, a salve or an ointment.

Collectively, or individually, the peptides of the present invention can be included in suspensions, solutions or oily emulsions in vehicles or in water and can contain useful suspending, stabilizing agents and/or agents promoting dispersion.

Collectively, or individually, the peptides of the present invention can be formulated in the form of a powder, obtained by aseptic isolation of a sterile solid or by freeze-drying a solution to be reconstituted in the form of a solution with the aid of a suitable vehicle before use, for example, water for injectable preparations.

Collectively, or individually, the peptides of the present invention can also be administered via the respiratory tract. For administration by inhalation or insufflation, the composition can be in the form of a dry powder, for example, a mixed powder of therapeutic agent and a suitable powdered basis, such as lactose or starch.

Collectively, or individually, the peptides of the present invention can be administered in an aqueous solution in the form of aerosol or by inhalatory route.

Throughout the description and claims of this specific invention, the words "comprise" and "contain" and variations of the words, for example "comprises" and "contains", mean "comprising but not limited to", and do not mean to exclude other fractions, additives, components or whole steps.

Throughout the description and claims of this specific invention below, the singular includes the plural, unless the context requires differently. Additionally, in those parts where the indefinite article is used, it is specifically to be meant as plurality and singularity, unless the context requires differently.

With "individually" or "individual" is meant that the invention comprises the mentioned antimicrobial peptide or groups of antimicrobial peptides, and that, although the single peptides or groups of peptides may not be listed separately here, the claims listed below can define such peptides or groups of peptides in a divisible way and separately the ones from the others.

With "collectively" or "collective" is meant that the invention includes any number or combination of mentioned antimicrobial peptides or groups of antimicrobial peptides, and that, it being understood that such numbers or combinations of peptides or groups of peptides cannot be specifically cited in the present document, the claims listed below can define such combinations or sub-combinations separately and in a divisible way from any other combination of peptides or groups of peptides.

The present invention is further described in the following and not limiting examples.

EXPERIMENTAL PART

Example 1

Synthesis of Peptides

Method

Synthesis of the peptides was performed by the company SelleckChem, through its associate in the United States. The synthesis was carried out by techniques known in the art and specifically by solid phase synthesis.

Results 100 peptides were synthesized, having length of 17 amino acids and a degree of purity comprised between 78 and 90%. The peptides were delivered in a 96-well plate containing 2-5 mg of freeze-dried peptide+4 cryovials containing the remaining 4 peptides. The technical report attached to the peptides did not highlight problems during the synthesis. In FIG. 1 the structure of the peptides is schematized.

Example 2

Membrane Permeabilization Assay Using the Bacterial Strain *E. coli* ML-35pYC

Methods

The strain ML-35pYC of *E. coli* was used to assay the kinetics of membrane permeabilization performed by the peptides of the invention. This bacterial strain expresses resistance to ampicillin, constitutive expression of cytoplasmic beta-galactosidase, and is engineered with a plasmid for the synthesis of a periplasmic beta-lactamase. Sixty microliters (60 µl) of bacterial suspension of strain ML-35pYC of *E. coli* were added to 60 µl of a 15 mM solution of ONPG or 1.5 mM of CENTA in phosphate buffer. Subsequently, 120 µl of the test peptides were added to obtain a final concentration of 12.5 µg/ml. The kinetics of the reaction was evaluated by recording the value of absorbance at 600 nm and 405 nm, for ONPG and CENTA respectively, every 10 min up to a maximum of 240 min.

Results

Figure 2A:
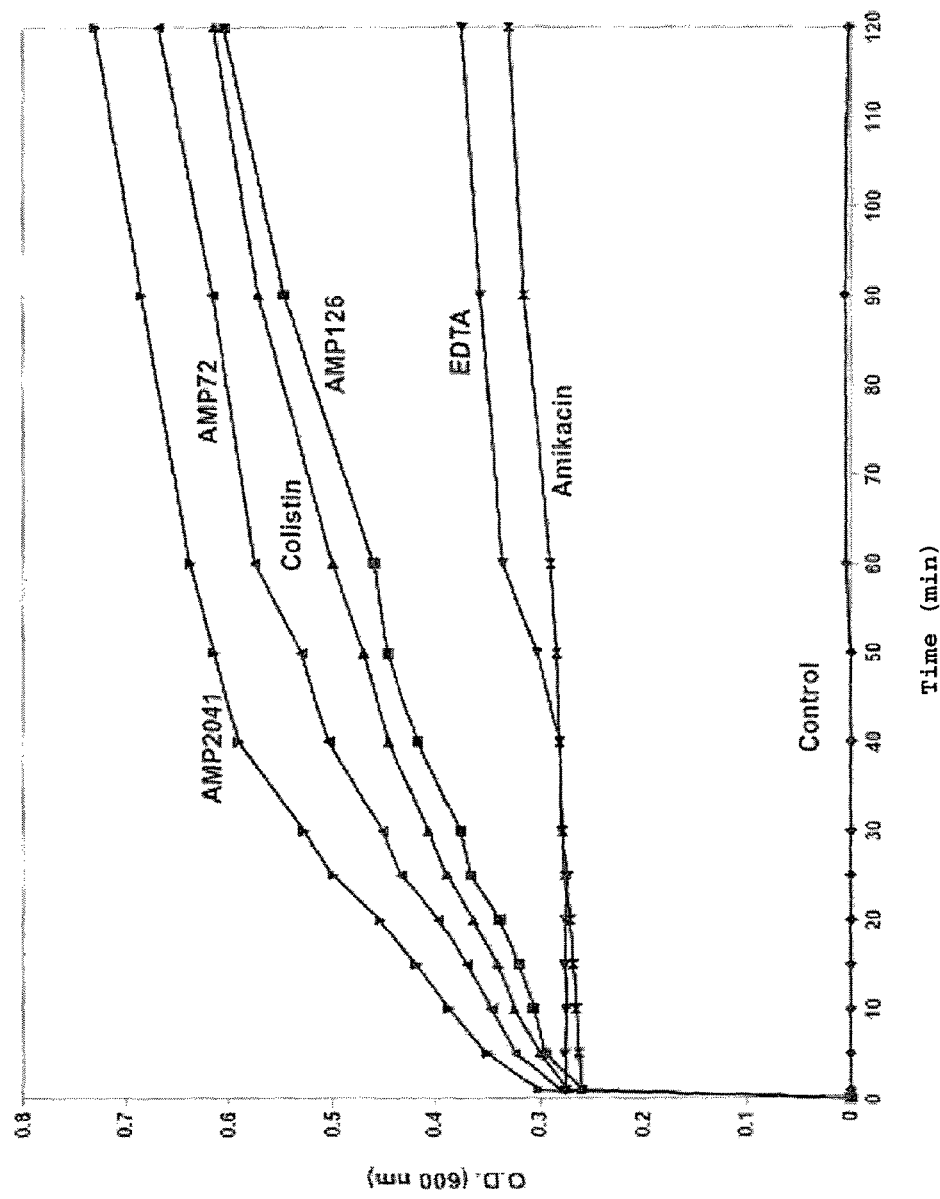
FIG. 2a: permeabilization curve of the membrane of *E. coli* ML35p by the peptides described in example 1. The increase of optical density is proportional to the concentration of cytoplasmic β-galactosidase released by damaged bacteria in the culture medium.
Figure 2B:
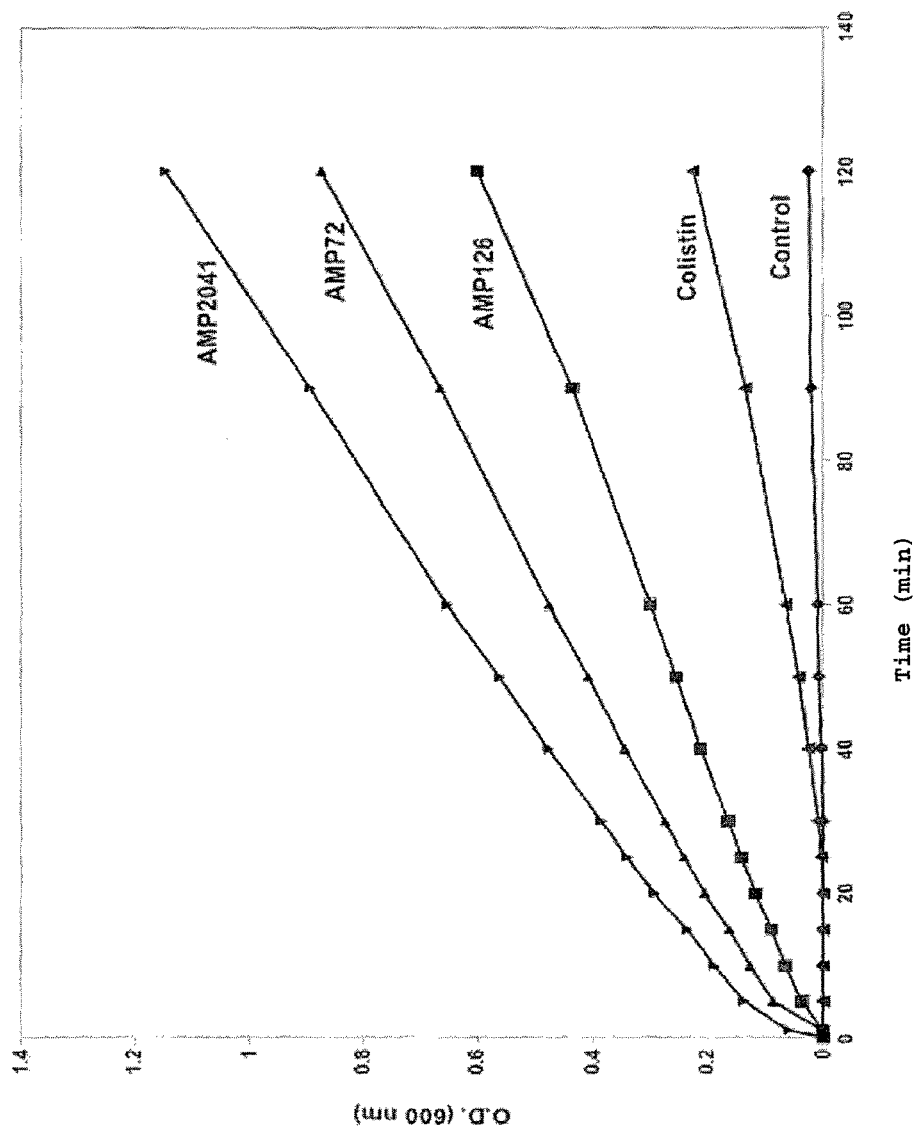
FIG. 2b: permeabilization curve of the membrane of *E. coli* ML35p by the peptides described in example 1. The increase of optical density is proportional to the concentration of a chromogenic derivative of the degradation of CENTA by a beta-lactamase released by damaged bacteria in the culture medium.

In FIGS. 2A and 2B the permeabilization curves relative to the 3 tested peptides are reported. When values of absorbance obtained with the assay using CENTA or ONPG are plotted versus time, it is possible to highlight two distinct behaviours.

By "fitting" the experimental points with the logistic 4-parameter curve, it was possible to determine the inflexion point, that is the point where the curve changes direction, relative to the 3 test peptides. No inflexion point was observed during the assay with CENTA (inflexion point higher than 500 min). The assay with ONPG emphasizes a plateau of absorbance after 40 min, and an inflexion point at 7.86 and 16.08 min, respectively for peptides P72 and P2041, while peptide 126 shows a linear trend for the whole duration of the experiment.

TABLE 1

Inflexion point obtained by fitting of experimental points with the logistic 4-parameter curve.

| Peptide | Inflexion point | |
|---|---|---|
| | CENTA | ONPG |
| 72 | >500 min | 7.86 min |
| 126 | >500 min | >500 min |
| 2041 | >500 min | 16.08 min |

Example 3

Determination of the Spectrum of Activity and Efficacy of Antimicrobial Peptides on Gram-Negative Bacteria This example demonstrates the spectrum of activity and efficacy of the tested peptides against *Escherichia coli* ATCC 25922, *Pseudomonas aeruginosa* ATCC 27853 and *Stenotrophomonas maltophilia* ATCC 13637. $LD_{90}$s were determined for each peptide and for each strain tested.

Methods a) Preparing the Bacterial Inoculum

For each bacterial strain, 3-5 morphologically similar colonies were drawn from fresh cultures, inoculated in Brain Hearth Infusion broth liquid medium and incubated at the temperature of 37° C. under shaking at 225 r.p.m. for 3-4 h. Subsequently, the bacterial suspension was centrifuged at 1000 g for 20 min and the thus obtained pellet was resuspended in phosphate buffer 10 mM. Turbidity was measured in a spectrophotometer with absorbance at 600 nm, equivalent in the range 0.08-0.13 to a concentration of about $10^8$ CFU/ml. The bacterial suspension was diluted 1:100 in phosphate buffer 10 mM, and within 30 min 50 microliters of such bacterial suspension ($10^6$ CFU/ml) were inoculated in each well of the microtiter plate, to obtain a final bacterial concentration of about $5 \times 10^5$ CFU/ml.

b) Serial Microdilution

Several peptides were tested for their ability to inhibit bacterial growth in liquid culture. Fifty microliters of peptide at a concentration comprised between about 0.2 mM and 50 mM were added in 96-well U-bottom plates containing liquid growth medium and one of the following bacteria: *Escherichia coli* ATCC 25922, *P. aeruginosa* ATCC 27853, *Stenotrophomonas maltophilia* ATCC 13637. After 2 hour incubation at 37° C., bacteria were transferred on a solid medium. As a growth control, bacterial cultures were cultured in the absence of peptides.

c) Transfer on Agar

The bacterial suspension was put in contact for two hours with different concentrations of the peptide at the temperature of 37° C. After incubation, 20 μl were drawn from the wells of each dilution and seeded on solid medium, agar McConkey. The inoculum was evenly distributed on the agarized medium by means of a sterile disposable loop. After incubation for 24 h at the temperature of 37° C., counting of the bacterial colonies (CFU) was performed.

Results

In table 2, $LD_{90}$ values for the different peptides are expressed. Peptides 72, 126 and 2041 result to be active against *E. coli* with an $LD_{90}$ value of 1.69 μg/ml (0.86 μM), 1.86 μg/ml (0.91 μM), 1.57 μg/ml (0.83 μM), respectively. Relative to *P. aeruginosa*, peptide 126 results to be the most efficient with an $LD_{90}$ value equal to 0.20 μM (0.4 μg/ml), followed by peptide 72 with an $LD_{90}$ value equal to 0.87 μM (1.61 μg/ml). Relative to *Stenotrophomonas maltophilia*, peptide 72 results to be the most efficient with an $LD_{90}$ value of 1.88 μM (3.42 μg/ml) followed by peptide 2041 with an $LD_{90}$ of 2.67 μM.

TABLE 2a

Antimicrobial activity. $LD_{90}$ Values obtained by broth-microdilution test and subsequent plating on agar.

| | Gram-negative bacteria | | |
| --- | --- | --- | --- |
| | *E. coli* ATCC 25922 | *P. aeruginosa* ATCC 27853 | *S. maltophilia* ATCC 13637 |
| P72 | 0.86 μM | 0.87 μM | 1.88 μM |
| P126 | 0.91 μM | 0.20 μM | 6.65 μM |
| P2041 | 0.83 μM | 2.14 μM | 2.67 μM |

Further tests, performed on the peptides according to the invention, provided the following results of antibacterial activity (MBC μg/ml).

TABLE 2b

Antimicrobial activity. MBC Values (μg/ml), obtained by the test of Table 2a. Antimicrobial activity. MBC Values (μg/ml) obtained by broth-microdilution test and subsequent plating on agar.

| | Gram-negative bacteria | |
| --- | --- | --- |
| | *E. coli* ATCC 25922 | *P. aeruginosa* ATCC 27853 |
| SEQ.ID.NO.: 1 | 3.05 | 2.08 |
| SEQ.ID.NO.: 2 | 9.68 | 2.84 |
| SEQ.ID.NO.: 3 | 12.5 | 4.53 |
| SEQ.ID.NO.: 4 | 17.37 | 1.14 |
| SEQ.ID.NO.: 5 | 1.08 | 1.09 |
| SEQ.ID.NO.: 22 | 11.72 | 1.08 |
| SEQ.ID.NO.: 8 | 9.26 | 1.81 |
| SEQ.ID.NO.: 7 | 7.81 | 3.4 |
| SEQ.ID.NO.: 6 | 1.81 | 0.4 |
| SEQ.ID.NO.: 9 | 7.56 | 2.57 |
| SEQ.ID.NO.: 10 | 24.6 | 12.08 |

Reference sequences, containing less than 5 points of alternation among the amino acids of group (a) and (b) in the tract comprised between the due cysteines (C),

P14: AKCRPLHTRGKQSAVCV

P127: FFCGNKRWRGNYQGSCK

P195: ANCWTRKIRGVVGVSCG tested in the same conditions, resulted inactive.

Example 4

Determination of the Spectrum of Activity and Efficacy of Antimicrobial Peptides on Gram-positive Bacteria This example demonstrates the spectrum of activity and efficacy of some antimicrobial peptides against strains of both meticillin-sensitive and meticillin-resistant (MRSA) *S. aureus*. For each peptide and for each strain $LD_{90}$ was determined.

Methods a) Preparing the Bacterial Inoculum

For each bacterial strain, 3-5 morphologically similar colonies were drawn from fresh cultures, inoculated in Brain Hearth Infusion broth liquid medium and incubated at the temperature of 37° C. under shaking at 225 r.p.m. for 3-4 h. Subsequently, the bacterial suspension was centrifuged at 1000 g for 20 min and the thus obtained pellet was resuspended in phosphate buffer 10 mM. Turbidity was measured in a spectrophotometer with absorbance at 600 nm, equivalent in the range 0.08-0.13 to a concentration of about $10^8$ CFU/ml. The bacterial suspension was diluted 1:100 in phosphate buffer 10 mM, and within 30 min, 50 microliters of such bacterial suspension ($10^6$ CFU/ml) were inoculated in each well of the microtiter plate, to obtain a final bacterial concentration of about $5 \times 10^5$ CFU/ml.

b) Serial Microdilution

Several synthetic peptides were tested for their ability to inhibit bacterial growth. Fifty microliters of peptide at a concentration comprised between about 0.2 mM and about 50 mM were added to 96-well U-bottom plates containing phosphate buffer and one of the following bacteria: *S. aureus* ATCC 25923, meticillin-resistant *S. aureus* ATCC 43300. After 2 hour incubation at 37° C., bacteria were transferred on a solid medium. As a control, the bacterial cultures were cultured in the absence of peptide.

c) Transfer on Agar

The bacterial suspension was put in contact for two hours with different concentrations of the peptide at the temperature of 37° C. After incubation, 20 μl were drawn from the wells of each dilution and seeded on solid medium, Columbia agar supplemented with 5% bovine red blood cells for Gram-positive bacteria. The inoculum was evenly distributed on the agarized medium by means of a sterile disposable loop. After incubation for 24 hours at the temperature of 37° C., counting of the bacterial colonies (CFU) was performed.

Results

In table 3, $LD_{90}$ values for the different peptides are expressed. Peptides 2041 and 72 result to be the most efficient against *S. aureus* ATCC 25923 with an $LD_{90}$ value of 1.42 μM (2.89 μg/ml) and 3.39 μM (6.16 μg/ml), respectively. Peptide 126 follows, with an $LD_{90}$ of 4.68 μM (9.54 μg/ml). Particularly interesting are the $LD_{90}$ values obtained in the case of meticillin-resistant *S. aureus* ATCC 43300. Relating to peptide 72 an $LD_{90}$ equal to 0.90 μM (1.65 μg/ml) was obtained, while with peptide 2041 a value of 0.85 μM (1.72 μg/ml). Peptide 126 has an $LD_{90}$ equal to about 71 μM (100 μg/ml).

TABLE 3

Antimicrobial activity. LD$_{90}$ Values obtained by broth-microdilution test and subsequent plating on agar.

| | Gram-positive bacteria | |
|---|---|---|
| | S. aureus ATCC 25923 | MRSA ATCC 43300 |
| P72 | 3.39 µM | 0.90 µM |
| P126 | 4.68 µM | >70 µM |
| P2041 | 1.42 µM | 0.85 µM |

TABLE 4

Antimicrobial activity. LD$_{90}$ Values obtained by broth-microdilution test and subsequent plating on agar.

| | Fungi (Yeasts) | |
|---|---|---|
| | Candida albicans | Malassezia pachydermatis |
| P72 | 1.03 µM | 0.68 µM |
| P126 | 1.98 µM | 0.75 µM |
| P2041 | 1.42 µM | 0.85 µM |

Example 5

Methodology for the Assay of Antimicrobial Activity of Peptides Against Fungal Strains (Yeasts)

Methods

The inoculum was set up by culturing *Candida albicans* ATCC 10231 and *Malassezia pachydermatis* ATCC 14522 in Czapek-Dox broth medium (DIFCO) for 48-72 h. On the assay day, the fungal culture was centrifuged at 1700×g for 15 min, the pellet was resuspended in phosphate buffer and submitted to shaking by the use of an electric vortex to disperse the fungal cell aggregates. The suspension was diluted until an optical density equal to an opacity of 0.5 on the McFarland turbidimetric scale was reached, which contains approximately 1-5×10$^6$ cell/ml (Branda J. A., Krantz A. Effectc of yeast on automated cell counting. Am J Clin Pathol., 2006:126, 248-254).

a) Serial Microdilution

The peptides were tested for their ability to inhibit fungal growth. Fifty microliters of peptide at a concentration comprised between about 0.2 mM and about 50 mM were added in 96-well U-bottom plates containing phosphate buffer and one of the following fungi: *Candida albicans* ATCC 10231 and *Malassezia pachydermatis* ATCC 14522. After 2 h incubation at 37° C., fungi were transferred on the solid medium agar Sabouraud. As a control, fungal cultures were cultured in the absence of peptide.

b) Transfer on Agar

The fungal suspension was put in contact for two hours with different concentrations of the peptide at the temperature of 37° C. After incubation, 20 µl were drawn from the wells of each dilution and seeded on the solid medium agar Sabouraud. The inoculum was evenly distributed on the agarized medium by means of a sterile disposable loop. After incubation for 24 h at the temperature of 37° C., counting of the fungal colonies (CFU) was performed.

Results

In table 4, LD$_{90}$ values for the different peptides are expressed. Peptide 72 resulted to be the most efficient against both fungal species tested. In particular, against *Candida albicans* a value of 1.03 µM (1.87 µg/ml) was obtained, while against *Malassezia* spp. 0.68 µM (1.24 µg/ml). For peptide 126 LD$_{90}$s ranged between a minimum of 0.75 µM and a maximum of about 2 µM for both fungal species tested.

Example 6

Cytotoxicity of the Antimicrobial Peptides

This example evaluates the cytotoxicity of antibacterial peptides by observing and quantifying haemolysis of red blood cells (RBC) of ram or the presence of intensely coloured cells with the vital stain Trypan Blue, in the presence and in the absence of peptide.

Methods (a) Haemolysis Test

Erythrocytes from ram, drawn immediately before the beginning of the test, were washed in isotonic buffer until the supernatant became clear. Washed erythrocytes were incubated with different concentrations of peptide for one hour at room temperature. After such period, the erythrocytes were pelletted by centrifugation. The supernatant was collected and analyzed at 450 nm for the quantification of haemolysis. Positive control consisted of lysated red blood cells with the addition of 0.1% Triton. This sample served for the determination of the maximal optical density. The percentage of haemolysis was calculated from the ratio between optical density of the sample and that of the positive control at 450 nm.

The MHC10 value was calculated as the minimum peptide concentration inducing 10% of cell lysis.

(b) Cytotoxicity of Peptides Against Jurkat Cells

Cytotoxicity of the peptides against T lymphocytes, for example Jurkat cells, was determined seeding the cells at a density of about 5*10$^5$ cells/ml in the presence and in the absence of peptides and incubating overnight at 37° C. in thermostat under CO$_2$. As a negative cytotoxicity control, a medium lacking the test peptide was used, while as a positive cytotoxicity control, a medium containing 0.2% Triton X-100 was used, to completely lyse the cells. The cell viability was subsequently determined by adding 20 µl of Trypan Blue in each well, and by incubation of the cells for additional 5 min a 37° C. MCC10 value was calculated as the minimum peptide concentration necessary to induce 10% of cytotoxicity.

Results

Figure 3:
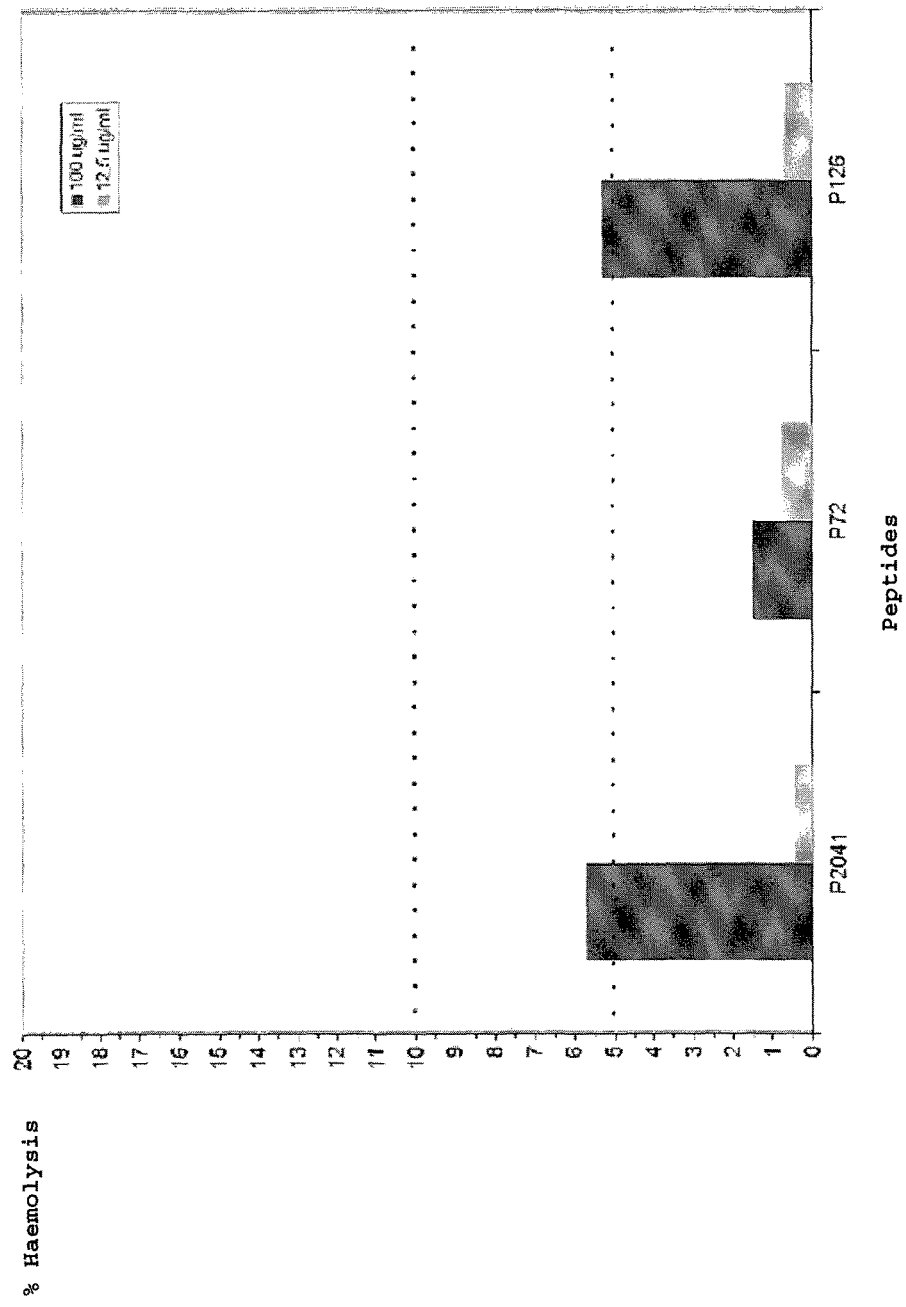
FIG. 3: haemolytic activity of peptides towards red blood cells from ram. The concentration tested is 20-fold $LD_{90}$. The percentage of haemolysis was calculated by analysis of optical density at 450 nm.

The data reported in FIG. 3 show the haemolytic activity of the tested peptides. All the peptides that have less than 10% of haemolytic activity at a concentration of 40 µM were considered not haemolytic. The data of haemolysis of these peptides resulted to be better than tachyplesin-1, that induced 15% of haemolysis of red blood cells at 40 µM.

The data presented in table 5 show the cytotoxicity of the peptides on Jurkat cells. All the peptides highlighted a cytotoxicity lower than 7% at 40 µM, and this confirms their lack of toxicity against eukaryotic cells. The data obtained are clearly favourable compared to those obtained with tachyplesin-1, that caused death of 10% of the cells at a concentration of 20 µM.

TABLE 5

| | Concentration (µg/ml) | |
| --- | --- | --- |
| | 100 µg/ml | 12.5 µg/ml |
| P72 | 6.02% | <3% |
| P126 | 5.04% | <2% |
| P2041 | 6.95% | <3% |

Example 7

Evaluation of Antimicrobial Activity in the Presence of Different Concentrations of Salt This example verifies the ability of the peptides to exert an antimicrobial activity in the presence of scalar concentrations of NaCl.

Methods a) Serial Microdilution

Several peptides were tested for their ability to inhibit bacterial growth in liquid culture. Fifty microliters of peptide at a concentration between about 0.2 mM and 50 mM were added in 96-well U-bottom plates containing phosphate buffer 10 mM supplemented with 125 or 250 mM NaCl and one of the following bacteria: Escherichia coli ATCC 25922, P. aeruginosa ATCC 27853. After 2 hour incubation at 37° C., bacteria were transferred on a solid medium. As a growth control, the bacterial cultures were cultured in the absence of peptides.

b) Transfer on Agar

The bacterial suspension was put in contact for two hours with different concentrations of the peptide at the temperature of 37° C. After incubation, 20 µl were drawn from the wells of each dilution and seeded on the solid medium agar McConkey for Gram-negative bacteria and Columbia agar supplemented with 5% bovine red blood cells for Gram-positive bacteria. The inoculum was evenly distributed on the agarized medium by means of a sterile disposable loop. After incubation for 24 h at the temperature of 37° C., counting of the colony forming units (CFU) was performed.

Results

In table 6A, the antimicrobial activity against E. coli ATCC 25922, Pseudomonas aeruginosa ATCC 27853 in the presence of 10 mM NaCl is reported. Activity was calculated as the percentage of CFU growth inhibition: for each peptide the amount of inhibition at the concentration of 100 and 12.5 µg/ml was evaluated.

At 10 mM NaCl, results are in accordance with what already previously obtained with the test described in example 3.

TABLE 6A

Antimicrobial activity (percentage in comparison with control) against E. coli, Pseudomonas aeruginosa in the presence of 10 mM NaCl.

| 10 mM | E. coli | | P. aeruginosa | |
| --- | --- | --- | --- | --- |
| ↓Peptide | 100 µg/ml* | 12.5 µg/ml | 100 µg/ml | 12.5 µg/ml |
| 72 | 100 | 100 | 100 | 100 |
| 126 | 100 | 99.68 | 100 | 100 |
| 2041 | 100 | 100 | 100 | 100 |

*tested concentration of the peptide

TABLE 6B

Antimicrobial activity against E. coli, P. aeruginosa in the presence of 125 mM NaCl.

| 125 mM | E. coli | | P. aeruginosa | |
| --- | --- | --- | --- | --- |
| ↓Peptide | 100 | 12.5 | 100 | 12.5 |
| 72 | 99.42 | 70.59 | 100 | 100 |
| 126 | 100 | 98.64 | 99.9 | 97.1 |
| 2041 | 100 | 99.95 | 100 | 100 |

In table 6B, the data of activity with 125 mM NaCl are reported. At this concentration of salt, peptide 2041 and peptide 126 demonstrate to completely retain their antimicrobial activity for the two Gram-negative bacteria. Peptide 72 results to be equally efficient at both concentrations for P. aeruginosa ATCC 27853.

TABLE 6C

Antimicrobial activity against E. coli, P. aeruginosa in the presence of 250 mM NaCl.

| 250 mM | E. coli | | P. aeruginosa | |
| --- | --- | --- | --- | --- |
| ↓Peptide | 100 | 12.5 | 100 | 12.5 |
| 72 | 44.64 | 25.8 | 80.5 | 64.28 |
| 126 | 90.6 | 86.7 | 98.1 | 85.2 |
| 2041 | 99.51 | 67.72 | 99.83 | 98.39 |

In table 6C, the activity data with 250 mM NaCl are reported. Although in these extreme conditions (concentration reachable only in certain pathological areas such as for example pulmonary fluid with cystic fibrosis) the different peptides tested still retain good/discrete antibacterial activity; particularly interesting is peptide 2041 that retains excellent activity against P. aeruginosa ATCC 27853 at both concentrations tested. Noteworthy is also the antibacterial activity higher than 85% of peptide 126 at the concentration of 12.5 µg/ml.

In additional experiments, the salt-resistance of peptides P944 and P1188 was tested, both containing a non-lipophylic amino acid at position 11. Both, while having a very good basal antibacterial activity, showed a very strong reduction of the same in the presence of increasing concentrations of salt. The percentages of growth inhibition depending on the concentration of salt present are as follows.

E. coli
(i) NaCl 10 mM
P944 100 µg/ml: 99.5%
P944 12.5 µg/ml: 95%
P1188 100 µg/ml: 100%
P1188 12.5 µg/ml: 95.3%
(ii) NaCl 125 mM
P944 100 µg/ml: 38.6%
P944 12.5 µg/ml: 36.6%
P1188 100 µg/ml: 52.4%
P1188 12.5 µg/ml: 45.3%
(iii) NaCl 250 mM
P944 100 µg/ml: 27%
P944 12.5 µg/ml: 28.5%
P1188 100 µg/ml: 38.3%
P1188 12.5 µg/ml: 25.3%
P. aeruginosa
(i) NaCl 10 mM
P944 100 µg/ml: 99.6%
P944 12.5 µg/ml: 95.8%

P1188 100 µg/ml: 99.2%
P1188 12.5 µg/ml: 97.3%
(ii) NaCl 125 mM
P944 100 µg/ml: 55.6%
P944 12.5 µg/ml: 46.6%
P1188 100 µg/ml: 60.3%
P1188 12.5 µg/ml: 55.3%
(iii) NaCl 250 mM
P944 100 µg/ml: 37.9%
P944 12.5 µg/ml: 35.4%
P1188 100 µg/ml: 15.3%
P1188 12.5 µg/ml: 10.3%

SEQUENCE LISTINGS PART OF THE DESCRIPTION

SEQ.ID.No.: 1
HIS*LYS*CYS*ALA*LYS*ILE*LYS*TRP*ARG*GLY*VAL*HIS*
VAL*LYS*TYR*CYS*ALA

SEQ.ID.No.: 2
LYS*GLY*CYS*ALA*LEU*VAL*LYS*VAL*ARG*GLY*LEU*THR*
LEU*LYS*VAL*CYS*LYS

SEQ.ID.No.: 3
LYS*TRP*CYS*ARG*LYS*TRP*GLN*TRP*ARG*GLY*VAL*LYS*
PHE*ILE*LYS*CYS*VAL

SEQ.ID.No.: 4
Ala*Ile*Cys*Arg*Thr*Trp*Lys*Tyr*Arg*Gly*His*Lys*
Trp*Lys*Ala*Cys*Lys*

SEQ.ID.No.: 5
Arg*Lys*Cys*Phe*Pro*Tyr*Arg*Phe*Arg*Gly*Lys*Arg*
Phe*Lys*Lys*Cys*Tyr*

SEQ.ID.No.: 6
Lys*Lys*Cys*Phe*Thr*Trp*Lys*Trp*Arg*Gly*Lys*Asn*
Tyr*Arg*Lys*Cys*Gly*

SEQ.ID.No.: 7
Arg*Gly*Cys*Trp*Arg*Trp*Lys*Trp*Arg*Gly*Val*Trp*
Tyr*Lys*Lys*Cys*Leu*

SEQ.ID.No.: 8
Gly*Lys*Cys*Trp*Lys*Trp*Lys*Tyr*Arg*Gly*His*Tyr*
Trp*Arg*Thr*Cys*Leu*

SEQ.ID.No.: 9
Lys*Asn*Cys*Leu*Lys*Trp*Lys*Trp*Arg*Gly*Ile*Thr*
Tyr*Arg*Lys*Cys*Leu*

SEQ.ID.No.: 10
Ile*Arg*Cys*Ala*Thr*Trp*Asn*Tyr*Arg*Gly*His*Gln*
Trp*Lys*Lys*Cys*Leu*

SEQ.ID.No.: 11
Gly*Asn*Cys*Lys*Val*Phe*Gln*Tyr*Arg*Gly*Lys*Arg*
Trp*Ala*Arg*Cys*Leu*

SEQ.ID.No.: 12
Leu*Gly*Cys*Lys*Arg*Phe*Lys*Phe*Arg*Gly*Ile*Thr*
Trp*Lys*Gly*Cys*Ile*

SEQ.ID.No.: 13
Leu*Thr*Cys*Arg*Lys*Trp*Tyr*Tyr*Arg*Gly*Val*His*
Trp*Lys*Val*Cys*Val*

SEQ.ID.No.: 14
Ala*Asn*Cys*Lys*Ile*Trp*Asn*Trp*Arg*Gly*Lys*Arg*
Tyr*Lys*Lys*Cys*Val*

SEQ.ID.No.: 15
Ile*Gly*Cys*Leu*Arg*Trp*Arg*Tyr*Arg*Gly*Val*Thr*
Trp*Arg*Lys*Cys*Val*

SEQ.ID.No.: 16
Lys*Asn*Cys*Ile*Lys*Tyr*His*Tyr*Arg*Gly*Ile*Asn*
Tyr*Arg*Ser*Cys*Gly*

SEQUENCE LISTINGS PART OF THE DESCRIPTION -continued

SEQ.ID.No.: 17
Lys*Lys*Cys*Gly*Ala*Phe*Thr*Tyr*Arg*Gly*Val*His*
Tyr*Arg*Lys*Cys*Val*

SEQ.ID.No.: 18
Ala*Val*Cys*Gly*Lys*Phe*His*Trp*Arg*Gly*Val*Lys*
Tyr*Arg*Ile*Cys*Lys*

SEQ.ID.No.: 19
Ala*Lys*Cys*Lys*Ser*Phe*Tyr*Tyr*Arg*Gly*Lys*Trp*
Phe*Gly*Lys*Cys*Tyr*

SEQ.ID.No.: 20
Lys*Trp*Cys*Arg*Val*Phe*His*Tyr*Arg*Gly*Asn*Lys*
Trp*Lys*Leu*Cys*Tyr*

SEQ.ID.No.: 21
Ala*Trp*Cys*Gly*Ala*Trp*Arg*Tyr*Arg*Gly*Lys*His*
Tyr*Ile*Lys*Cys*Arg*

SEQ.ID.No.: 22
Arg*Asn*Cys*Leu*Lys*Trp*Thr*Trp*Arg*Gly*Ile*Thr*
Tyr*Leu*Lys*Cys*Lys*

SEQ.ID.No.: 23
Ala*Ile*Cys*Arg*Ala*Tyr*Lys*Tyr*Arg*Gly*His*Lys*
Trp*Gly*Ile*Cys*Ala*

SEQ.ID.No.: 24
Lys*Lys*Cys*Ala*Leu*Trp*Lys*Phe*Arg*Gly*His*Lys*
Trp*Val*a*rgCys*Ala*

SEQ.ID.No.: 25
Leu*Leu*Cys*Leu*Lys*Trp*Lys*Tyr*Arg*Gly*His*Thr*
Tyr*Arg*Gly*Cys*Leu*

SEQ.ID.No.: 26
Leu*Lys*Cys*Ile*Gly*Trp*Thr*Tyr*Arg*Gly*His*Lys*
Trp*Arg*Ser*Cys*Phe*

SEQ.ID.No.: 27
Lys*Lys*Cys*Lys*Gly*Tyr*Trp*Trp*Arg*Gly*Val*
a*rgTyr*Lys*Ile*Cys*Lys*

SEQ.ID.No.: 28
Ala*Gly*Cys*Lys*Ile*Tyr*Arg*Trp*Arg*Gly*His*Thr*
Trp*Lys*Ile*Cys*Gly*

SEQ.ID.No.: 29
Phe*Lys*Cys*Gly*Ala*Trp*His*Tyr*Arg*Gly*Asn*Arg*
Trp*Val*Lys*Cys*Leu*

SEQ.ID.No.: 30
Ile*Trp*Cys*Leu*Arg*Trp*His*Tyr*Arg*Gly*Lys*Lys*
Tyr*Ala*Val*Cys*Ala*

SEQ.ID.No.: 31
Ile*Arg*Cys*Lys*Lys*Tyr*Ser*Phe*Arg*Gly*Val*His*
Tyr*Val*Ser*Cys*Ala*

SEQ.ID.No.: 32
Gly*Asn*Cys*Lys*Gly*Tyr*His*Trp*Arg*Gly*His*Lys*
Phe*Lys*Leu*Cys*Leu*

SEQ.ID.No.: 33
Phe*Leu*Cys*Lys*Ser*Trp*Lys*Trp*Arg*Gly*Lys*Tyr*
Tyr*Ile*Arg*Cys*Leu*

SEQ.ID.No.: 34
Gly*Leu*Cys*Arg*Leu*Tyr*Lys*Tyr*Arg*Gly*Val*Lys*
Tyr*Lys*Ser*Cys*Leu*

SEQ.ID.No.: 35
Lys*Trp*Cys*Ile*Lys*Phe*Ser*Tyr*Arg*Gly*Ile*Trp*
Trp*Lys*Ala*Cys*Arg*

SEQUENCE LISTINGS PART OF THE DESCRIPTION

SEQ.ID.No.: 36
Leu*Lys*Cys*Gly*Thr*Trp*Arg*Phe*Arg*Gly*His*Lys*
Trp*Lys*Val*Cys*Tyr*

SEQ.ID.No.: 37
Leu*Lys*Cys*Lys*Val*Tyr*Arg*Phe*Arg*Gly*Ile*Arg*
Tyr*Gly*Lys*Cys*Leu*

SEQ.ID.No.: 38
Ala*Phe*Cys*Ala*Lys*Tyr*Arg*Phe*Arg*Gly*Lys*Arg*
Tyr*Val*Gly*Cys*Ala*

SEQ.ID.No.: 39
Lys*Asn*Cys*Phe*Lys*Trp*Thr*Tyr*Arg*Gly*His*Tyr*
Trp*Lys*Ser*Cys*Ala*

SEQ.ID.No.: 40
Lys*Leu*Cys*Lys*Leu*Tyr*Thr*Tyr*Arg*Gly*Lys*Tyr*
Trp*Gly*Lys*Cys*Lys*

SEQ.ID.No.: 41
Ala*Lys*Cys*Ala*Arg*Tyr*Asn*Tyr*Arg*Gly*Lys*Lys*
Trp*Leu*Lys*Cys*Arg*

SEQ.ID.No.: 42
Phe*Gly*Cys*Arg*Lys*Phe*Tyr*Trp*Arg*Gly*Val*Lys*
Trp*Lys*Val*Cys*Ala*

SEQ.ID.No.: 43
Gly*Ile*Cys*Lys*Thr*Trp*Asn*Tyr*Arg*Gly*Lys*Lys*
Tyr*Lys*Ile*Cys*Leu*

SEQ.ID.No.: 44
Arg*Asn*Cys*Ala*Phe*Trp*Lys*Trp*Arg*Gly*Lys*Ser*
Tyr*Ala*Leu*Cys*Lys*

SEQ.ID.No.: 45
Lys*Ile*Cys*Ala*Lys*Tyr*Asn*Trp*Arg*Gly*Lys*Thr*
Tyr*Lys*Ile*Cys*Leu*

SEQ.ID.No.: 46
Ala*lle*Cys*Ala*Arg*Trp*Lys*Trp*Arg*Gly*Ile*Ser*
Tyr*Lys*Arg*Cys*Arg*

SEQ.ID.No.: 47
Ile*Phe*Cys*Trp*Gly*Tyr*Lys*Phe*Arg*Gly*Val*His*
Tyr*Lys*Ala*Cys*Arg*

SEQ.ID.No.: 48
Lys*Thr*Cys*Ala*Lys*Trp*Ser*Tyr*Arg*Gly*Val*
a*snTyr*Gly*Arg*Cys*Arg*

SEQ.ID.No.: 49
Ala*Lys*Cys*Ser*Val*Tyr*Thr*Trp*Arg*Gly*Asn*Lys*
Trp*Arg*Thr*Cys*Lys*

SEQ.ID.No.: 50
Ile*Arg*Cys*Ala*Val*Trp*Lys*Tyr*Arg*Gly*Asn*Lys*
Tyr*Lys*Thr*Cys*Ala*

SEQ.ID.No.: 51
Lys*Leu*Cys*Lys*Thr*Trp*Gln*Trp*Arg*Gly*His*Thr*
Trp*Arg*Thr*Cys*Ile*

SEQ.ID.No.: 52
Lys*Ile*Cys*Gly*Lys*Tyr*His*Phe*Arg*Gly*Val*Gln*
Tyr*Lys*Ala*Cys*Lys*

SEQ.ID.No.: 53
Lys*Lys*Cys*Lys*Ala*Tyr*Thr*Phe*Arg*Gly*Val*Tyr*
Trp*Lys*Ala*Cys*Leu*

SEQ.ID.No.: 54
Leu*Lys*Cys*Arg*Thr*Trp*Asn*Trp*Arg*Gly*Lys*Lys*
Tyr*Ala*Leu*Cys*Lys*

The invention claimed is:

1. A peptide consisting of a sequence A-B-C-D-C'-B'-A', wherein: units A and A' consist independently of 1 or 2 amino acids; units B and B' consist independently of an amino acid containing sulfur; at least one of units C and C' comprises Lys and units C and C' consist independently of 5 amino acids, selected both in group (a) of hydrophobic amino acids, and in group (b) of basic amino acids or amino acids forming hydrogen bonds; unit D consists of arginine-glycine, further wherein:
  (i) said hydrophobic amino acids are selected from: Ala, Phe, Ile, Leu, Pro, Tyr, Trp and Val;
  (ii) said basic amino acids are selected from: Lys, His, and Arg;
  (iii) said amino acids forming hydrogen bonds are selected from: Asn, Gln, Ser, and Thr;
  and wherein the substructure C-D-C' as a whole contains 5 to 9 points of alternation between amino acid of group (a) and amino acid of group (b), or vice versa; and
  further wherein the peptide is in the cyclized form via formation of a disulfide bridge between units B and B'.

2. The peptide according to claim 1, wherein both units C and C' comprise Lys.

3. The peptide according to claim 1, wherein the amino acid adjacent to Gly of unit D is a hydrophobic amino acid.

4. The peptide according to claim 3, wherein the amino acid adjacent to Gly of unit D is a hydrophobic aromatic amino acid.

5. The peptide according to claim 1, wherein units A and A' comprise, independently one from another, one or more amino acids selected: from His, Lys, Gly, Tyr, Ala, and Val.

6. The peptide according to claim 1, selected from SEQ ID NOS:1-54.

7. The peptide according to claim 6, selected from SEQ ID NOS:1-3.

8. A pharmaceutical composition for use in humans or animals, comprising a peptide according to claim 1 and a suitable excipient.

9. The pharmaceutical composition according to claim 8, suitable for topical, oral, subcutaneous, parenteral or inhalatory administration.

10. A method of treating an infection caused by a bacterium, a fungus, or a yeast, comprising the step of administering a peptide according to claim 1 to a subject of need thereof.

11. The method according to claim 10, wherein said infection is caused by an organism selected from the group of organisms consisting of *Staphylococcus, Enterococcus, Pseudomonas, Mycobacterium, Enterobacter, Campylobacter, Salmonella, Streptococcus, Helicobacter, Neisseria, Borrelia burgdorferi, Shigella, Escherichia, Haemophilus, Francisella tularensis, Bacillus, Clostridia, Yersinia, Treponema, Burkholderia, Stenotrophomonas, Candida, Epidermophyton, Exophiala, Microsporum, Trichophyton, Tinea, Aspergillus, Blastomyces, Blastoschizomyces, Coccidioides, Cryptococcus, Histoplasma, Paracoccidiomyces, Sporotrix, Absidz, Cladophialophora, Fonsecaea, Phialophora, Lacazia, Arirographis, Acremonium, Actinomadura, Apophysomyces, Emmonsia, Basidiobolus, Beauveria, Chrysosporium, Conidiobolus, Cunninghamella, Fusarium, Geotrichum, Graphium, Leptosphaeria, Malassezia, Mucor., Neotestudina, Nocardia, Nocardiopsis, Paecilomyces, Phoma, Piedraia, Pneumocystis, Pseudallescheria, Pyrenochaeta, Rhizomucor, Rhizopus, Rhodotorula, Saccharorraces, Scedosporium, Scopulariopsis, Sporobolomyces, Syncephalastrum, Trichoderma, Trichosporon, Ulocladium, Ustilago, Verticillium,* and *Wangiella.*

12. The method according to claim 11, wherein: the *Staphylococcus* is *Staphylococcus aureus* or *Staphylococcus aureus* ATCC 25923; the *Enterococcus* is *Enterococcus faecalis*; the *Pseudomonas* is *Pseudomonas aeruginosa* ATCC 27853; the *Mycobacterium* is *Mycobacterium tuberculosis*; the *Streptococcus* is *Streptococcus* group A, *Streptococcus* group B, or *Streptoccocus pneumoniae*; the *Helicobacter* is *Helicobacter pylori*; the *Neisseria* is *Neisseria gonorrea* or *Neisseria meningitidis*; the *Shigella* is *Shigella flexneri*; the *Escherichia* is *Escherichia coli* ATCC 25922; the *Haemophilus* is *Haemophilus influenzae*; the *Bacillus* is *Bacillus anthracis*; the *Clostridia* is *Clostridium botulinum*; the *Yersinia* is *Yersinia pestis*; the *Burkholderia* is *Burkholderia cepacia, Burkholderia mallei,* or *Burkholderia pseudomallei*; the *Stenotrophomonas* is *Stenotrophomonas maltophilei*; the *Candida* is *Candida albicans,* the *Trichophyton* is *Trichophyton rubrum* or *Trichophyton interdigitale*; the *Cryptococcus* is *Cryptococcus neoformans*; and the *Malassezia* is *Malassezia furfur.*

13. A process to synthesize a peptide according to claim 1, comprising coupling in linear sequence all the amino acids forming said structure A-B-C-D-C'-B'-A'.

* * * * *

SEQUENCE LISTING

<160> NUMBER OF SEQ ID NOS: 54

<210> SEQ ID NO 1
<211> LENGTH: 17
<212> TYPE: PRT
<213> ORGANISM: Unknown
<220> FEATURE:
<223> OTHER INFORMATION: Recombinant synthetic protein

<400> SEQUENCE: 1

His Lys Cys Ala Lys Ile Lys Trp Arg Gly Val His Val Lys Tyr Cys
1               5                   10                  15

Ala

<210> SEQ ID NO 2

```
<211> LENGTH: 17
<212> TYPE: PRT
<213> ORGANISM: Unknown
<220> FEATURE:
<223> OTHER INFORMATION: Recombinant synthetic protein

<400> SEQUENCE: 2

Lys Gly Cys Ala Leu Val Lys Val Arg Gly Leu Thr Leu Lys Val Cys
1               5                   10                  15

Lys

<210> SEQ ID NO 3
<211> LENGTH: 17
<212> TYPE: PRT
<213> ORGANISM: Unknown
<220> FEATURE:
<223> OTHER INFORMATION: Recombinant synthetic protein

<400> SEQUENCE: 3

Lys Trp Cys Arg Lys Trp Gln Trp Arg Gly Val Lys Phe Ile Lys Cys
1               5                   10                  15

Val

<210> SEQ ID NO 4
<211> LENGTH: 17
<212> TYPE: PRT
<213> ORGANISM: Unknown
<220> FEATURE:
<223> OTHER INFORMATION: Recombinant synthetic protein

<400> SEQUENCE: 4

Ala Ile Cys Arg Thr Trp Lys Tyr Arg Gly His Lys Trp Lys Ala Cys
1               5                   10                  15

Lys

<210> SEQ ID NO 5
<211> LENGTH: 17
<212> TYPE: PRT
<213> ORGANISM: Unknown
<220> FEATURE:
<223> OTHER INFORMATION: Recombinant synthetic protein

<400> SEQUENCE: 5

Arg Lys Cys Phe Pro Tyr Arg Phe Arg Gly Lys Arg Phe Lys Lys Cys
1               5                   10                  15

Tyr

<210> SEQ ID NO 6
<211> LENGTH: 17
<212> TYPE: PRT
<213> ORGANISM: Unknown
<220> FEATURE:
<223> OTHER INFORMATION: Recombinant synthetic protein

<400> SEQUENCE: 6

Lys Lys Cys Phe Thr Trp Lys Trp Arg Gly Lys Asn Tyr Arg Lys Cys
1               5                   10                  15

Gly

<210> SEQ ID NO 7
<211> LENGTH: 17
<212> TYPE: PRT
<213> ORGANISM: Unknown
<220> FEATURE:
```

-continued

<223> OTHER INFORMATION: Recombinant synthetic protein

<400> SEQUENCE: 7

Arg Gly Cys Trp Arg Trp Lys Trp Arg Gly Val Trp Tyr Lys Lys Cys
1               5                   10                  15
Leu

<210> SEQ ID NO 8
<211> LENGTH: 17
<212> TYPE: PRT
<213> ORGANISM: Unknown
<220> FEATURE:
<223> OTHER INFORMATION: Recombinant synthetic protein

<400> SEQUENCE: 8

Gly Lys Cys Trp Lys Trp Lys Tyr Arg Gly His Tyr Trp Arg Thr Cys
1               5                   10                  15
Leu

<210> SEQ ID NO 9
<211> LENGTH: 17
<212> TYPE: PRT
<213> ORGANISM: Unknown
<220> FEATURE:
<223> OTHER INFORMATION: Recombinant synthetic protein

<400> SEQUENCE: 9

Lys Asn Cys Leu Lys Trp Lys Trp Arg Gly Ile Thr Tyr Arg Lys Cys
1               5                   10                  15
Leu

<210> SEQ ID NO 10
<211> LENGTH: 17
<212> TYPE: PRT
<213> ORGANISM: Unknown
<220> FEATURE:
<223> OTHER INFORMATION: Recombinant synthetic protein

<400> SEQUENCE: 10

Ile Arg Cys Ala Thr Trp Asn Tyr Arg Gly His Gln Trp Lys Lys Cys
1               5                   10                  15
Leu

<210> SEQ ID NO 11
<211> LENGTH: 17
<212> TYPE: PRT
<213> ORGANISM: Unknown
<220> FEATURE:
<223> OTHER INFORMATION: Recombinant synthetic protein

<400> SEQUENCE: 11

Gly Asn Cys Lys Val Phe Gln Tyr Arg Gly Lys Arg Trp Ala Arg Cys
1               5                   10                  15
Leu

<210> SEQ ID NO 12
<211> LENGTH: 17
<212> TYPE: PRT
<213> ORGANISM: Unknown
<220> FEATURE:
<223> OTHER INFORMATION: Recombinant synthetic protein

<400> SEQUENCE: 12

```
Leu Gly Cys Lys Arg Phe Lys Phe Arg Gly Ile Thr Trp Lys Gly Cys
1               5                   10                  15

Ile
```

<210> SEQ ID NO 13
<211> LENGTH: 17
<212> TYPE: PRT
<213> ORGANISM: Unknown
<220> FEATURE:
<223> OTHER INFORMATION: Recombinant synthetic protein

<400> SEQUENCE: 13

```
Leu Thr Cys Arg Lys Trp Tyr Tyr Arg Gly Val His Trp Lys Val Cys
1               5                   10                  15

Val
```

<210> SEQ ID NO 14
<211> LENGTH: 17
<212> TYPE: PRT
<213> ORGANISM: Unknown
<220> FEATURE:
<223> OTHER INFORMATION: Recombinant synthetic protein

<400> SEQUENCE: 14

```
Ala Asn Cys Lys Ile Trp Asn Trp Arg Gly Lys Arg Tyr Lys Lys Cys
1               5                   10                  15

Val
```

<210> SEQ ID NO 15
<211> LENGTH: 17
<212> TYPE: PRT
<213> ORGANISM: Unknown
<220> FEATURE:
<223> OTHER INFORMATION: Recombinant synthetic protein

<400> SEQUENCE: 15

```
Ile Gly Cys Leu Arg Trp Arg Tyr Arg Gly Val Thr Trp Arg Lys Cys
1               5                   10                  15

Val
```

<210> SEQ ID NO 16
<211> LENGTH: 17
<212> TYPE: PRT
<213> ORGANISM: Unknown
<220> FEATURE:
<223> OTHER INFORMATION: Recombinant synthetic protein

<400> SEQUENCE: 16

```
Lys Asn Cys Ile Lys Tyr His Tyr Arg Gly Ile Asn Tyr Arg Ser Cys
1               5                   10                  15

Gly
```

<210> SEQ ID NO 17
<211> LENGTH: 17
<212> TYPE: PRT
<213> ORGANISM: Unknown
<220> FEATURE:
<223> OTHER INFORMATION: Recombinant synthetic protein

<400> SEQUENCE: 17

```
Lys Lys Cys Gly Ala Phe Thr Tyr Arg Gly Val His Tyr Arg Lys Cys
1               5                   10                  15

Val
```

<210> SEQ ID NO 18
<211> LENGTH: 17
<212> TYPE: PRT
<213> ORGANISM: Unknown
<220> FEATURE:
<223> OTHER INFORMATION: Recombinant synthetic protein

<400> SEQUENCE: 18

Ala Val Cys Gly Lys Phe His Trp Arg Gly Val Lys Tyr Arg Ile Cys
1               5                   10                  15

Lys

<210> SEQ ID NO 19
<211> LENGTH: 17
<212> TYPE: PRT
<213> ORGANISM: Unknown
<220> FEATURE:
<223> OTHER INFORMATION: Recombinant synthetic protein

<400> SEQUENCE: 19

Ala Lys Cys Lys Ser Phe Tyr Tyr Arg Gly Lys Trp Phe Gly Lys Cys
1               5                   10                  15

Tyr

<210> SEQ ID NO 20
<211> LENGTH: 17
<212> TYPE: PRT
<213> ORGANISM: Unknown
<220> FEATURE:
<223> OTHER INFORMATION: Recombinant synthetic protein

<400> SEQUENCE: 20

Lys Trp Cys Arg Val Phe His Tyr Arg Gly Asn Lys Trp Lys Leu Cys
1               5                   10                  15

Tyr

<210> SEQ ID NO 21
<211> LENGTH: 17
<212> TYPE: PRT
<213> ORGANISM: Unknown
<220> FEATURE:
<223> OTHER INFORMATION: Recombinant synthetic protein

<400> SEQUENCE: 21

Ala Trp Cys Gly Ala Trp Arg Tyr Arg Gly Lys His Tyr Ile Lys Cys
1               5                   10                  15

Arg

<210> SEQ ID NO 22
<211> LENGTH: 17
<212> TYPE: PRT
<213> ORGANISM: Unknown
<220> FEATURE:
<223> OTHER INFORMATION: Recombinant synthetic protein

<400> SEQUENCE: 22

Arg Asn Cys Leu Lys Trp Thr Trp Arg Gly Ile Thr Tyr Leu Lys Cys
1               5                   10                  15

Lys

<210> SEQ ID NO 23
<211> LENGTH: 17

<212> TYPE: PRT
<213> ORGANISM: Unknown
<220> FEATURE:
<223> OTHER INFORMATION: Recombinant synthetic protein

<400> SEQUENCE: 23

Ala Ile Cys Arg Ala Tyr Lys Tyr Arg Gly His Lys Trp Gly Ile Cys
1               5                   10                  15

Ala

<210> SEQ ID NO 24
<211> LENGTH: 17
<212> TYPE: PRT
<213> ORGANISM: Unknown
<220> FEATURE:
<223> OTHER INFORMATION: Recombinant synthetic protein

<400> SEQUENCE: 24

Lys Lys Cys Ala Leu Trp Lys Phe Arg Gly His Lys Trp Val Arg Cys
1               5                   10                  15

Ala

<210> SEQ ID NO 25
<211> LENGTH: 17
<212> TYPE: PRT
<213> ORGANISM: Unknown
<220> FEATURE:
<223> OTHER INFORMATION: Recombinant synthetic protein

<400> SEQUENCE: 25

Leu Leu Cys Leu Lys Trp Lys Tyr Arg Gly His Thr Tyr Arg Gly Cys
1               5                   10                  15

Leu

<210> SEQ ID NO 26
<211> LENGTH: 17
<212> TYPE: PRT
<213> ORGANISM: Unknown
<220> FEATURE:
<223> OTHER INFORMATION: Recombinant synthetic protein

<400> SEQUENCE: 26

Leu Lys Cys Ile Gly Trp Thr Tyr Arg Gly His Lys Trp Arg Ser Cys
1               5                   10                  15

Phe

<210> SEQ ID NO 27
<211> LENGTH: 17
<212> TYPE: PRT
<213> ORGANISM: Unknown
<220> FEATURE:
<223> OTHER INFORMATION: Recombinant synthetic protein

<400> SEQUENCE: 27

Lys Lys Cys Lys Gly Tyr Trp Trp Arg Gly Val Arg Tyr Lys Ile Cys
1               5                   10                  15

Lys

<210> SEQ ID NO 28
<211> LENGTH: 17
<212> TYPE: PRT
<213> ORGANISM: Unknown
<220> FEATURE:
<223> OTHER INFORMATION: Recombinant synthetic protein

```
<400> SEQUENCE: 28

Ala Gly Cys Lys Ile Tyr Arg Trp Arg Gly His Thr Trp Lys Ile Cys
1               5                   10                  15
Gly

<210> SEQ ID NO 29
<211> LENGTH: 17
<212> TYPE: PRT
<213> ORGANISM: Unknown
<220> FEATURE:
<223> OTHER INFORMATION: Recombinant synthetic protein

<400> SEQUENCE: 29

Phe Lys Cys Gly Ala Trp His Tyr Arg Gly Asn Arg Trp Val Lys Cys
1               5                   10                  15
Leu

<210> SEQ ID NO 30
<211> LENGTH: 17
<212> TYPE: PRT
<213> ORGANISM: Unknown
<220> FEATURE:
<223> OTHER INFORMATION: Recombinant synthetic protein

<400> SEQUENCE: 30

Ile Trp Cys Leu Arg Trp His Tyr Arg Gly Lys Lys Tyr Ala Val Cys
1               5                   10                  15
Ala

<210> SEQ ID NO 31
<211> LENGTH: 17
<212> TYPE: PRT
<213> ORGANISM: Unknown
<220> FEATURE:
<223> OTHER INFORMATION: Recombinant synthetic protein

<400> SEQUENCE: 31

Ile Arg Cys Lys Lys Tyr Ser Phe Arg Gly Val His Tyr Val Ser Cys
1               5                   10                  15
Ala

<210> SEQ ID NO 32
<211> LENGTH: 17
<212> TYPE: PRT
<213> ORGANISM: Unknown
<220> FEATURE:
<223> OTHER INFORMATION: Recombinant synthetic protein

<400> SEQUENCE: 32

Gly Asn Cys Lys Gly Tyr His Trp Arg Gly His Lys Phe Lys Leu Cys
1               5                   10                  15
Leu

<210> SEQ ID NO 33
<211> LENGTH: 17
<212> TYPE: PRT
<213> ORGANISM: Unknown
<220> FEATURE:
<223> OTHER INFORMATION: Recombinant synthetic protein

<400> SEQUENCE: 33

Phe Leu Cys Lys Ser Trp Lys Trp Arg Gly Lys Tyr Tyr Ile Arg Cys
```

```
1               5                   10                  15

Leu

<210> SEQ ID NO 34
<211> LENGTH: 17
<212> TYPE: PRT
<213> ORGANISM: Unknown
<220> FEATURE:
<223> OTHER INFORMATION: Recombinant synthetic protein

<400> SEQUENCE: 34

Gly Leu Cys Arg Leu Tyr Lys Tyr Arg Gly Val Lys Tyr Lys Ser Cys
1               5                   10                  15

Leu

<210> SEQ ID NO 35
<211> LENGTH: 17
<212> TYPE: PRT
<213> ORGANISM: Unknown
<220> FEATURE:
<223> OTHER INFORMATION: Recombinant synthetic protein

<400> SEQUENCE: 35

Lys Trp Cys Ile Lys Phe Ser Tyr Arg Gly Ile Trp Trp Lys Ala Cys
1               5                   10                  15

Arg

<210> SEQ ID NO 36
<211> LENGTH: 17
<212> TYPE: PRT
<213> ORGANISM: Unknown
<220> FEATURE:
<223> OTHER INFORMATION: Recombinant synthetic protein

<400> SEQUENCE: 36

Leu Lys Cys Gly Thr Trp Arg Phe Arg Gly His Lys Trp Lys Val Cys
1               5                   10                  15

Tyr

<210> SEQ ID NO 37
<211> LENGTH: 17
<212> TYPE: PRT
<213> ORGANISM: Unknown
<220> FEATURE:
<223> OTHER INFORMATION: Recombinant synthetic protein

<400> SEQUENCE: 37

Leu Lys Cys Lys Val Tyr Arg Phe Arg Gly Ile Arg Tyr Gly Lys Cys
1               5                   10                  15

Leu

<210> SEQ ID NO 38
<211> LENGTH: 17
<212> TYPE: PRT
<213> ORGANISM: Unknown
<220> FEATURE:
<223> OTHER INFORMATION: Recombinant synthetic protein

<400> SEQUENCE: 38

Ala Phe Cys Ala Lys Tyr Arg Phe Arg Gly Lys Arg Tyr Val Gly Cys
1               5                   10                  15

Ala
```

<210> SEQ ID NO 39
<211> LENGTH: 17
<212> TYPE: PRT
<213> ORGANISM: Unknown
<220> FEATURE:
<223> OTHER INFORMATION: Recombinant synthetic protein

<400> SEQUENCE: 39

Lys Asn Cys Phe Lys Trp Thr Tyr Arg Gly His Tyr Trp Lys Ser Cys
1               5                   10                  15

Ala

<210> SEQ ID NO 40
<211> LENGTH: 17
<212> TYPE: PRT
<213> ORGANISM: Unknown
<220> FEATURE:
<223> OTHER INFORMATION: Recombinant synthetic protein

<400> SEQUENCE: 40

Lys Leu Cys Lys Leu Tyr Thr Tyr Arg Gly Lys Tyr Trp Gly Lys Cys
1               5                   10                  15

Lys

<210> SEQ ID NO 41
<211> LENGTH: 17
<212> TYPE: PRT
<213> ORGANISM: Unknown
<220> FEATURE:
<223> OTHER INFORMATION: Recombinant synthetic protein

<400> SEQUENCE: 41

Ala Lys Cys Ala Arg Tyr Asn Tyr Arg Gly Lys Lys Trp Leu Lys Cys
1               5                   10                  15

Arg

<210> SEQ ID NO 42
<211> LENGTH: 17
<212> TYPE: PRT
<213> ORGANISM: Unknown
<220> FEATURE:
<223> OTHER INFORMATION: Recombinant synthetic protein

<400> SEQUENCE: 42

Phe Gly Cys Arg Lys Phe Tyr Trp Arg Gly Val Lys Trp Lys Val Cys
1               5                   10                  15

Ala

<210> SEQ ID NO 43
<211> LENGTH: 17
<212> TYPE: PRT
<213> ORGANISM: Unknown
<220> FEATURE:
<223> OTHER INFORMATION: Recombinant synthetic protein

<400> SEQUENCE: 43

Gly Ile Cys Lys Thr Trp Asn Tyr Arg Gly Lys Lys Tyr Lys Ile Cys
1               5                   10                  15

Leu

<210> SEQ ID NO 44
<211> LENGTH: 17
<212> TYPE: PRT

```
<213> ORGANISM: Unknown
<220> FEATURE:
<223> OTHER INFORMATION: Recombinant synthetic protein

<400> SEQUENCE: 44

Arg Asn Cys Ala Phe Trp Lys Trp Arg Gly Lys Ser Tyr Ala Leu Cys
1               5                   10                  15

Lys

<210> SEQ ID NO 45
<211> LENGTH: 17
<212> TYPE: PRT
<213> ORGANISM: Unknown
<220> FEATURE:
<223> OTHER INFORMATION: Recombinant synthetic protein

<400> SEQUENCE: 45

Lys Ile Cys Ala Lys Tyr Asn Trp Arg Gly Lys Thr Tyr Lys Ile Cys
1               5                   10                  15

Leu

<210> SEQ ID NO 46
<211> LENGTH: 17
<212> TYPE: PRT
<213> ORGANISM: Unknown
<220> FEATURE:
<223> OTHER INFORMATION: Recombinant synthetic protein

<400> SEQUENCE: 46

Ala Ile Cys Ala Arg Trp Lys Trp Arg Gly Ile Ser Tyr Lys Arg Cys
1               5                   10                  15

Arg

<210> SEQ ID NO 47
<211> LENGTH: 17
<212> TYPE: PRT
<213> ORGANISM: Unknown
<220> FEATURE:
<223> OTHER INFORMATION: Recombinant synthetic protein

<400> SEQUENCE: 47

Ile Phe Cys Trp Gly Tyr Lys Phe Arg Gly Val His Tyr Lys Ala Cys
1               5                   10                  15

Arg

<210> SEQ ID NO 48
<211> LENGTH: 17
<212> TYPE: PRT
<213> ORGANISM: Unknown
<220> FEATURE:
<223> OTHER INFORMATION: Recombinant synthetic protein

<400> SEQUENCE: 48

Lys Thr Cys Ala Lys Trp Ser Tyr Arg Gly Val Asn Tyr Gly Arg Cys
1               5                   10                  15

Arg

<210> SEQ ID NO 49
<211> LENGTH: 17
<212> TYPE: PRT
<213> ORGANISM: Unknown
<220> FEATURE:
<223> OTHER INFORMATION: Recombinant synthetic protein
```

```
<400> SEQUENCE: 49

Ala Lys Cys Ser Val Tyr Thr Trp Arg Gly Asn Lys Trp Arg Thr Cys
1               5                   10                  15

Lys

<210> SEQ ID NO 50
<211> LENGTH: 17
<212> TYPE: PRT
<213> ORGANISM: Unknown
<220> FEATURE:
<223> OTHER INFORMATION: Recombinant synthetic protein

<400> SEQUENCE: 50

Ile Arg Cys Ala Val Trp Lys Tyr Arg Gly Asn Lys Tyr Lys Thr Cys
1               5                   10                  15

Ala

<210> SEQ ID NO 51
<211> LENGTH: 17
<212> TYPE: PRT
<213> ORGANISM: Unknown
<220> FEATURE:
<223> OTHER INFORMATION: Recombinant synthetic protein

<400> SEQUENCE: 51

Lys Leu Cys Lys Thr Trp Gln Trp Arg Gly His Thr Trp Arg Thr Cys
1               5                   10                  15

Ile

<210> SEQ ID NO 52
<211> LENGTH: 17
<212> TYPE: PRT
<213> ORGANISM: Unknown
<220> FEATURE:
<223> OTHER INFORMATION: Recombinant synthetic protein

<400> SEQUENCE: 52

Lys Ile Cys Gly Lys Tyr His Phe Arg Gly Val Gln Tyr Lys Ala Cys
1               5                   10                  15

Lys

<210> SEQ ID NO 53
<211> LENGTH: 17
<212> TYPE: PRT
<213> ORGANISM: Unknown
<220> FEATURE:
<223> OTHER INFORMATION: Recombinant synthetic protein

<400> SEQUENCE: 53

Lys Lys Cys Lys Ala Tyr Thr Phe Arg Gly Val Tyr Trp Lys Ala Cys
1               5                   10                  15

Leu

<210> SEQ ID NO 54
<211> LENGTH: 17
<212> TYPE: PRT
<213> ORGANISM: Unknown
<220> FEATURE:
<223> OTHER INFORMATION: Recombinant synthetic protein
```

```
<400> SEQUENCE: 54

Leu Lys Cys Arg Thr Trp Asn Trp Arg Gly Lys Lys Tyr Ala Leu Cys
1               5                   10                  15
Lys
```